United States Patent
Greenhalgh et al.

(10) Patent No.: US 8,382,842 B2
(45) Date of Patent: Feb. 26, 2013

(54) EXPANDABLE SUPPORT DEVICE AND METHOD OF USE

(75) Inventors: E. Skott Greenhalgh, Perkasie, PA (US); John-Paul Romano, Chalfont, PA (US)

(73) Assignee: Stout Medical Group, L.P., Perkasie, PA (US)

(*) Notice: Subject to any disclaimer, the term of this patent is extended or adjusted under 35 U.S.C. 154(b) by 178 days.

(21) Appl. No.: 12/780,744

(22) Filed: May 14, 2010

(65) Prior Publication Data

US 2010/0292796 A1 Nov. 18, 2010

Related U.S. Application Data

(60) Provisional application No. 61/178,355, filed on May 14, 2009.

(51) Int. Cl.
A61F 2/44 (2006.01)
(52) U.S. Cl. .................. 623/17.16; 623/17.11
(58) Field of Classification Search ...... 623/17.11–17.16
See application file for complete search history.

(56) References Cited

U.S. PATENT DOCUMENTS

| | | | |
|---|---|---|---|
| 3,604,414 A | 9/1971 | Borges | |
| 3,659,595 A | 5/1972 | Haboush | |
| 5,616,142 A | 4/1997 | Yuan et al. | |
| 5,672,177 A | 9/1997 | Seldin | |
| 5,827,286 A | 10/1998 | Incavo et al. | |
| 5,895,387 A | 4/1999 | Guerrero et al. | |
| 5,964,763 A | 10/1999 | Incavo et al. | |
| 6,093,188 A | 7/2000 | Murray | |
| 6,402,756 B1 | 6/2002 | Ralph et al. | |
| 6,503,250 B2 | 1/2003 | Paul | |
| 6,679,883 B2 | 1/2004 | Hawkes et al. | |
| 6,689,134 B2 | 2/2004 | Ralph et al. | |
| 6,719,796 B2 | 4/2004 | Cohen et al. | |
| 6,852,113 B2 | 2/2005 | Nathanson et al. | |
| 6,932,820 B2 | 8/2005 | Osman | |
| 7,118,573 B2 | 10/2006 | Michelson | |
| 7,137,984 B2 | 11/2006 | Michelson | |
| 7,214,243 B2 * | 5/2007 | Taylor | 623/17.11 |
| 2002/0188296 A1 | 12/2002 | Michelson | |
| 2004/0019353 A1 | 1/2004 | Freid et al. | |
| 2004/0092939 A1 | 5/2004 | Freid et al. | |

(Continued)

FOREIGN PATENT DOCUMENTS

WO WO 2004/110300 12/2004
WO WO 2006/042334 4/2006

(Continued)

OTHER PUBLICATIONS

Franklin, I.J. et al., "Uptake of Tetracycline by Aortic Aneurysm Wall and Its Effect on Inflammation and Proteolysis," *Brit. J. Surger*, 86(6)771-775, 1999.

(Continued)

*Primary Examiner* — Kevin T Truong
*Assistant Examiner* — Christian Sevilla
(74) *Attorney, Agent, or Firm* — Levine Bagade Han LLP

(57) ABSTRACT

An expandable support device for tissue repair is disclosed. The device can be used to repair hard or soft tissue, such as bone or vertebral discs. A method of repairing tissue is also disclosed. The device and method can be used to treat compression fractures. The compression fractures can be in the spine. The device can be deployed by compressing the device longitudinally resulting in radial expansion.

8 Claims, 22 Drawing Sheets

U.S. PATENT DOCUMENTS

| | | |
|---|---|---|
| 2004/0153065 A1 | 8/2004 | Lim |
| 2004/0162618 A1 | 8/2004 | Mujwid et al. |
| 2005/0043732 A1 | 2/2005 | Dalton |
| 2005/0209698 A1 | 9/2005 | Gordon et al. |
| 2005/0240184 A1 | 10/2005 | Osman |
| 2006/0015103 A1 | 1/2006 | Burke |
| 2006/0116683 A1 | 6/2006 | Barrall et al. |
| 2006/0129244 A1 | 6/2006 | Ensign |
| 2006/0235398 A1 | 10/2006 | Farris et al. |
| 2006/0276794 A1 | 12/2006 | Stern |
| 2010/0145386 A1 | 6/2010 | Greenhalgh et al. |

FOREIGN PATENT DOCUMENTS

| | | |
|---|---|---|
| WO | WO 2006/068682 | 6/2006 |

OTHER PUBLICATIONS

Pyo, R. et al., "Targeted Gene Disruption of Matrix Metalloproteinase-9 (Gelatinase B) Suppresses Development of Experimental Abdominal Aortic Aneurysms," *J. Clinical Investigation*, 105(11);1641-1649, Jun. 2000.

Tambiah, J. et al., "Provocation of Experimental Aortic Inflammation Mediators and *Chlamydia pneumoniae*," *Brit., J. Surgery*, 88(7):935-940, Feb. 2001.

Walton, L.J. et al., "Inhibition of Prostoglandin E2 Synthesis in Abdonminal Aortic Aneurysms," *Circulation*, 48-54, Jul. 6, 1999.

Xu, Q. et al., "Sp1 Increases Expression of Cyclooxygenase-2 in Hypoxic Vascular Endothelium," *J. Biological Chemistry*, 275(32):24583-24589, Aug. 2000.

* cited by examiner

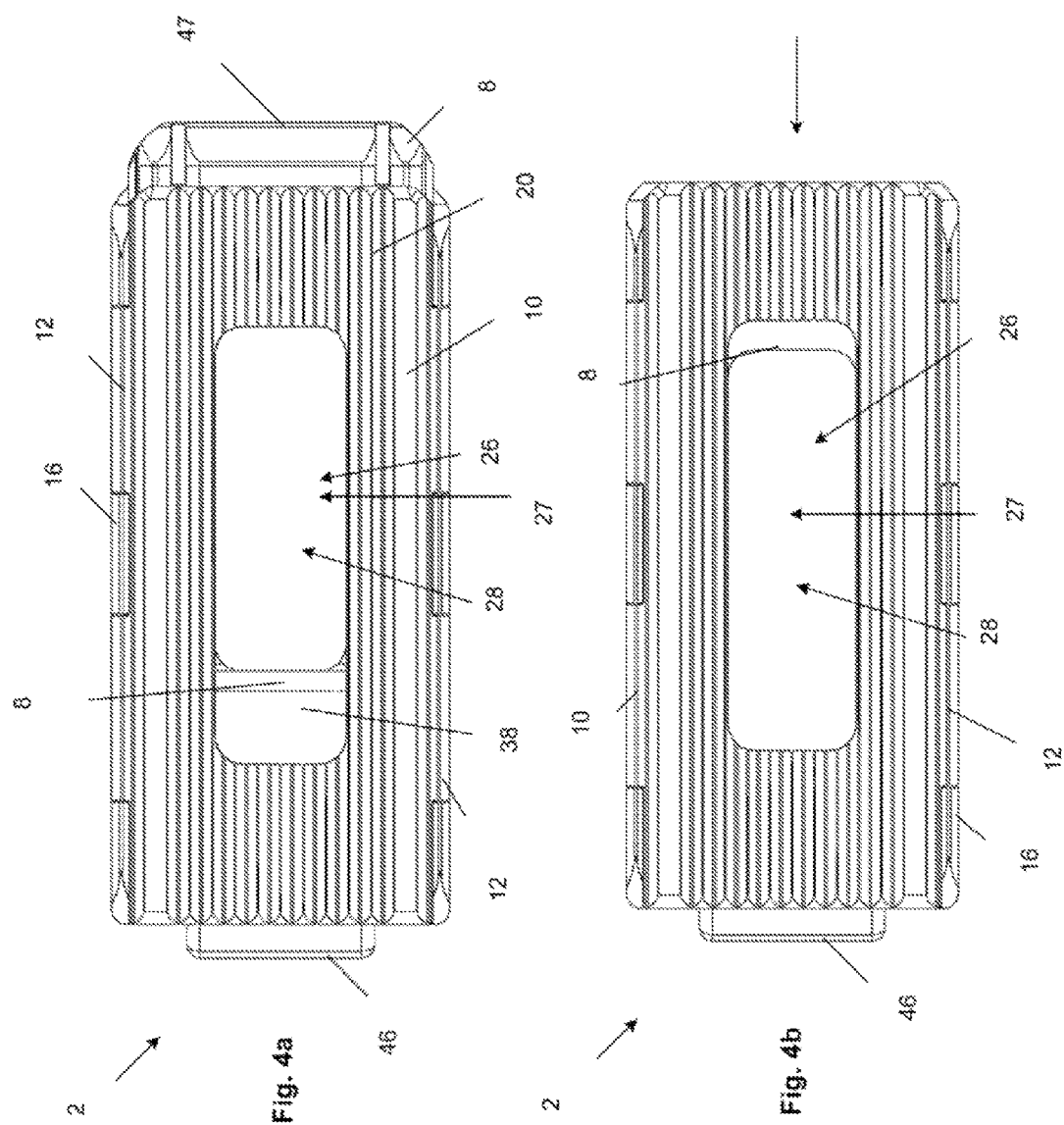

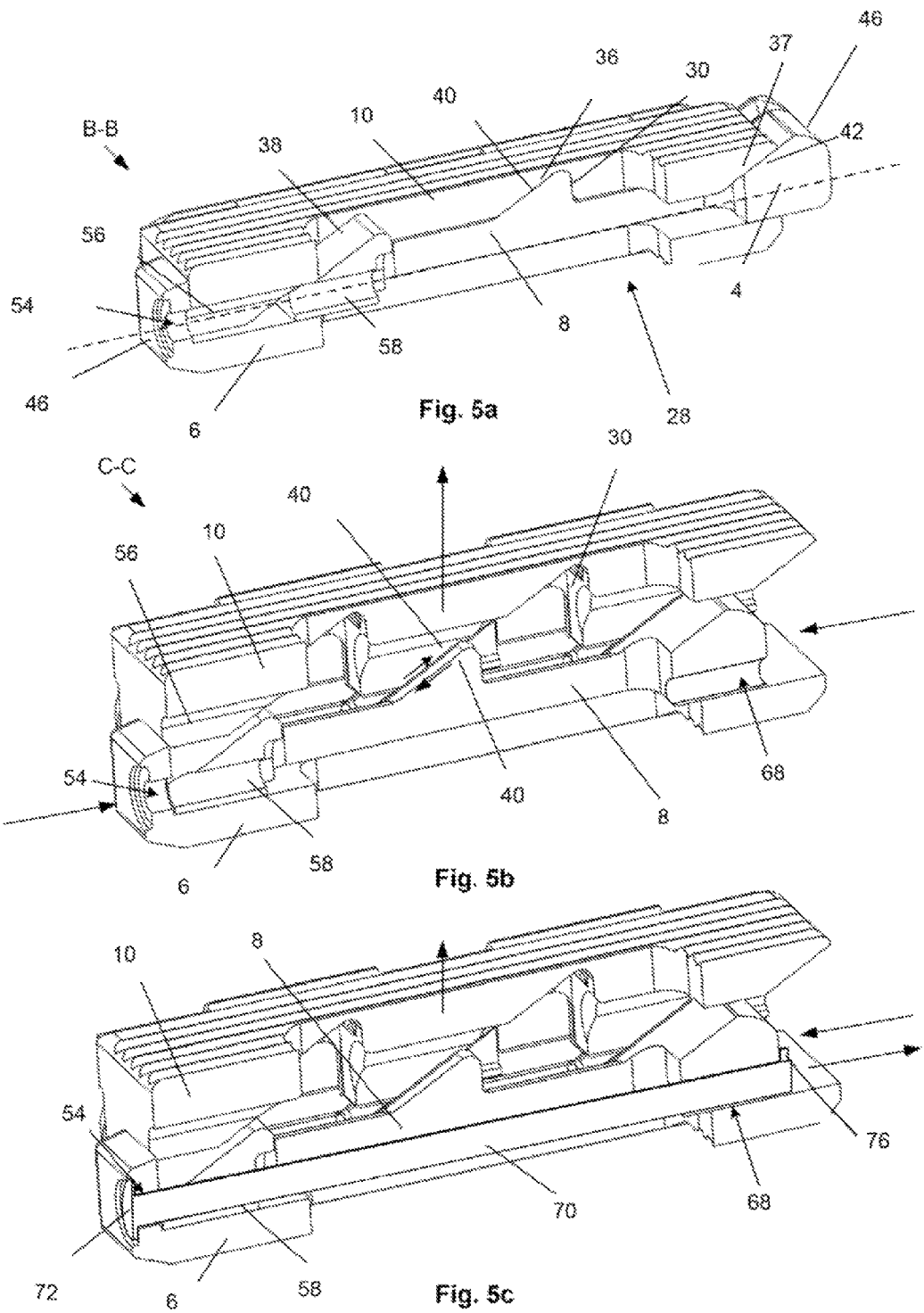

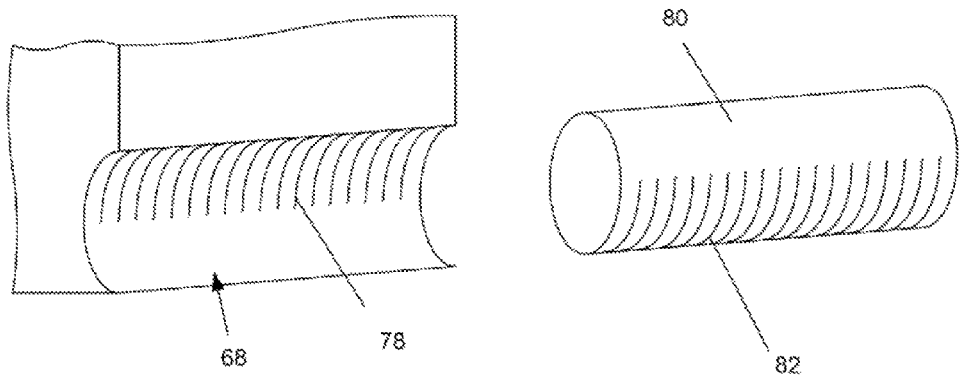
Fig. 5e
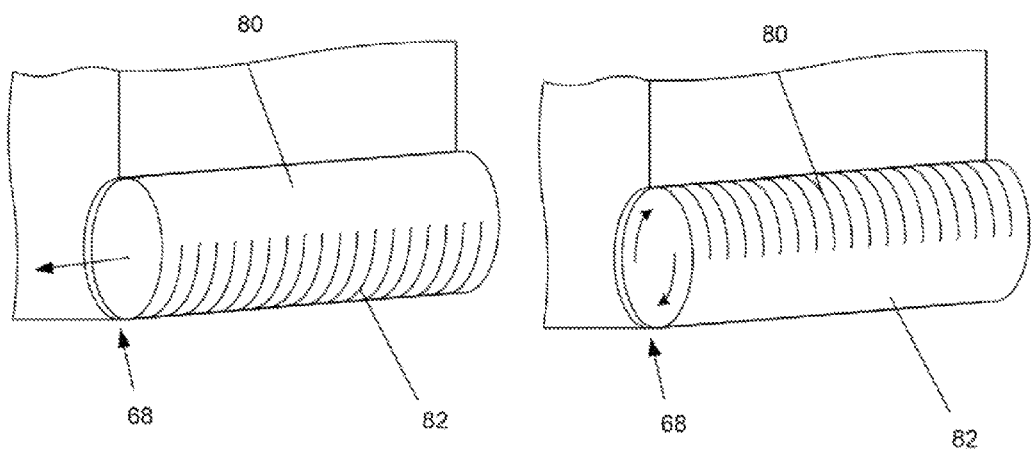
Fig. 5f
Fig. 5g

EXPANDABLE SUPPORT DEVICE AND METHOD OF USE

CROSS-REFERENCE TO RELATED APPLICATIONS

This application claims the benefit of U.S. Provisional Application No. 61/178,355, filed 14 May 2009, which is herein incorporated by reference in its entirety.

BACKGROUND OF THE INVENTION

1. Field of the Invention

This invention relates to devices for providing support for biological tissue, for example to fuse vertebral bodies, repair herniated discs, and/or repair spinal compression fractures, and methods of using the same.

2. Description of Related Art

Some conditions of the spine result from degradation or injury to the bone structures of the spine, typically the vertebral body. These can be the result of bone degeneration such as through osteoporosis or trauma, such as compression fractures. breakdown or injury to the boney structures in the spine can result in pain and spinal deformity with comorbidities.

Vertebroplasty is an image-guided, minimally invasive, nonsurgical therapy used to strengthen a broken vertebra that has been weakened by disease, such as osteoporosis or cancer. Vertebroplasty is often used to treat compression fractures, such as those caused by osteoporosis, cancer, or stress.

Vertebroplasty is often performed on patients too elderly or frail to tolerate open spinal surgery, or with bones too weak for surgical spinal repair. Patients with vertebral damage due to a malignant tumor may sometimes benefit from vertebroplasty. The procedure can also be used in younger patients whose osteoporosis is caused by long-term steroid treatment or a metabolic disorder.

Vertebroplasty can increase the patient's functional abilities, allow a return to the previous level of activity, and prevent further vertebral collapse. Vertebroplasty attempts to also alleviate the pain caused by a compression fracture.

Vertebroplasty is often accomplished by injecting an orthopedic cement mixture through a needle into the fractured bone. The cement mixture can leak from the bone, potentially entering a dangerous location such as the spinal canal. The cement mixture, which is naturally viscous, is difficult to inject through small diameter needles, and thus many practitioners choose to "thin out" the cement mixture to improve cement injection, which ultimately exacerbates the leakage problems. The flow of the cement liquid also naturally follows the path of least resistance once it enters the bone— naturally along the cracks formed during the compression fracture. This further exacerbates the leakage.

The mixture also fills or substantially fills the cavity of the compression fracture and is limited to certain chemical composition, thereby limiting the amount of otherwise beneficial compounds that can be added to the fracture zone to improve healing. In an alternative procedure known as kyphoplasty, a balloon is first inserted in the compression fracture and the vertebra and is expanded to create a void before the cement is injected into the newly formed space.

A vertebroplasty device and method that eliminates or reduces the risks and complexity of the existing art is desired. A vertebroplasty device and method that may reduce or eliminate the need to inject a liquid directly into the compression fracture zone is also desired.

Other ailments of the spine result in degeneration of the spinal disc in the intervertebral space between the vertebral bodies. These include degenerative disc disease and traumatic injuries. In either case, disc degeneration can cause pain and other complications. Conservative treatment can include non-operative treatment requiring patients to adjust their lifestyles and submit to pain relievers and a level of underlying pain. Operative treatment options include disc removal. This can relieve pain in the short term, but also often increases the risk of long-term problems and can result in motor and sensory deficiencies resulting from the surgery. Disc removal and more generally disc degeneration disease are likely to lead to a need for surgical treatment in subsequent years. The fusion or fixation will minimize or substantially eliminate relative motion between the fixed or fused vertebrae. In surgical treatments, adjacent vertebra can be fixated or fused to each other using devices or bone grafts. These may include, for example, screw and rod systems, interbody spacers (e.g., PEEK spacers or allograft bone grafts) threaded fusion cages and the like.

Some fixation or fusion devices are attached to the vertebra from the posterior side. The device will protrude and result in additional length (i.e., needed to overlap the vertebrae) and additional hardware to separately attach to each vertebrae. Fusion cages and allografts are contained within the intervertebral space, but must be inserted into the intervertebral space in the same dimensions as desired to occupy the intervertebral space. This requires that an opening sufficient to allow the cage or graft must be created through surrounding tissue to permit the cage or graft to be inserted into the intervertebral space.

A spinal fixation or fusion device that can be implanted with or without the need for additional hardware is desired. Also desired is a fixation or fusion device that can be deployed in a configuration where overlapping the fixated or fused vertebrae is not required.

Also desired is an intervertebral device the may be inserted in to the intervertebral space at a first smaller dimension and deployed to a second, larger dimension to occupy the intervertebral space. The ability to insert an intervertebral spacer at a dimension smaller than the deployed dimension would permit less disruption of soft and boney tissue in order to access the intervertebral space.

An effective therapy for following up a discectomy is desired. A vertebral fusion technique that can be used subsequent to a discectomy is desired.

SUMMARY OF THE INVENTION

An expandable support device that can be used to repair fractures and stabilize hard tissue, such as via intravertebral or intervertebral deployment; is disclosed. The expandable support device can have a longitudinal axis and a radial axis. The expandable support device can be configured to expand in a radial direction, for example constrained to expansion in a single dimension. The expansion can occur perpendicular to the longitudinal axis of the device. The device can have top and/or middle and/or bottom components. The top and/or middle and/or bottom components can have ramps or wedges that produce an opposing force to expand the device when the top and/or middle and/or bottom components are translated relative to each other in the longitudinal direction. For example, the device can expand radially (e.g., solely in height or width) when compressed longitudinally.

The device can be configured to expand in a single direction. The device can be configured to expand in two directions.

The device can have a locking pin. The locking pin can be interference fit with the device, for example with the first strut, and/or with a longitudinal port of the device.

Methods for deploying an expandable support device in the spine are disclosed. The expandable support device can be deployed, for example, by longitudinal compression. The longitudinal compression can result in radial expansion of the expandable support device. The expandable support device can be deployed in an intravertebral site. The expandable support device can be deployed in an intervertebral site.

Tools for deploying the expandable support device can be configured to apply a compressive force on the expandable support device along the expandable support device's longitudinal axis. The tools can be configured to securely engage the expandable support device. The tools can be configured to removably attach to opposing points at or near opposing longitudinal ends of the expandable support device. Actuation of the tool to apply a compressive force may include squeezing two handles together or rotating a knob or handle.

The expandable device can be filled with a material, such as a biocompatible material such as a bone morphogenic protein, bone cement or any other material listed herein and combinations thereof. For example, when used to treat compression fractures, a material such bone cement, tissue or bone growth factors, bone morphogenic proteins, stem cells, carriers for any of the foregoing, or mixtures thereof can be inserted within the expandable device to provide support, fixation and/or improved bone structure. Growth factors or stem cells can be obtained autologously, such as from the patient's own blood or bone marrow aspirate. The expandable device can be filled with autograft, allograft, bone extenders (e.g., calcium phosphate or tricalcium phosphate or mixtures thereof or other similar materials), bone growth factors, bone morphogenic proteins, stem cells, carriers for any of the foregoing, and mixtures thereof, for example, when the device is used as an intervertebral spacer for fusion. The growth factors and stem cells used can be those commercially available and/or can be extracted from the patient's own blood or bone marrow aspirate.

In addition, the ratio of the expansion for the expandable devices (the ratio of the unexpanded height or diameter, depending on configuration, to the expanded height or diameter) may be from 1:2 to 1:5 or greater. For intravertebral and intervertebral applications, the device can have expansion ratios of from about 1:3 to about 1:4. For vertebroplasty or interbody applications, the device can have an initial height or diameter from about 4 mm (0.16 in.) to about 8 mm (0.31 in.) and an expanded height or diameter from about 7 mm (0.28 in.) to about 18 mm (0.71 in.).

BRIEF DESCRIPTION OF THE DRAWINGS

FIG. 1b is a variation of cross-section 1a.

FIG. 2b is a variation of cross-section B-B of FIG. 2a.

FIG. 3b is a variation of cross-section C-C of FIG. 3a.

FIG. 4a is a top view of a variation of the device in a height-contracted configuration.

FIG. 4b is a top view of a variation of the device in a height-expanded.

FIGS. 5a and 5b illustrate a variation of a method of expanding the device, shown in cross-sections B-B and C-C, respectively, of FIGS. 2a and 3a.

FIG. 5c and 5d illustrate variations of a method for using the device having a variation of a cross-section C-C of FIG. 3a with a deployment tool and/or locking rod.

FIGS. 5e through 5g are a close up view of a method of using the deployment rod or locking pin with the second side port shown in a cross-sectional view.

DETAILED DESCRIPTION

Figure 1A:
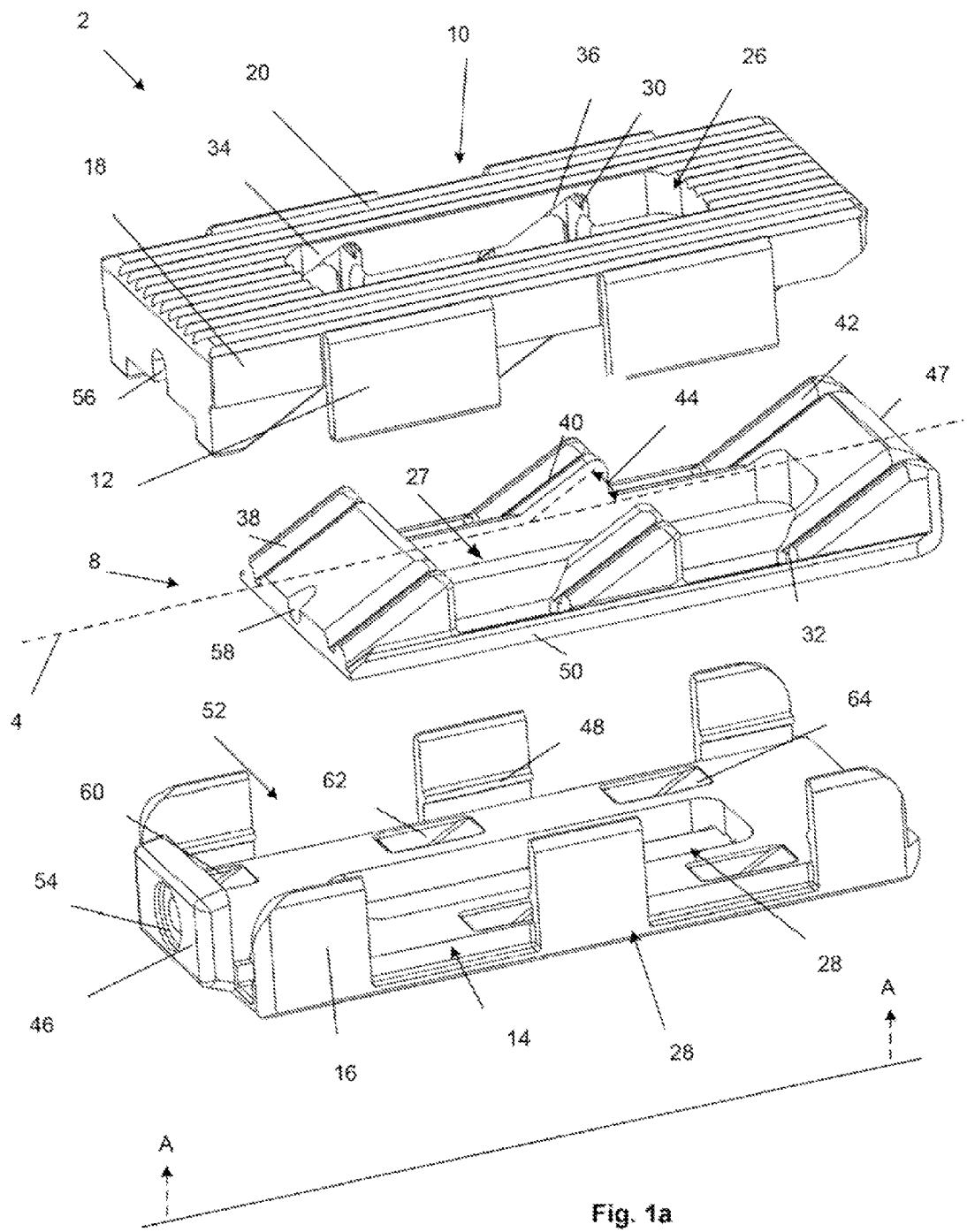
FIG. 1a illustrates an exploded view of a variation of the device.
Figure 1B:
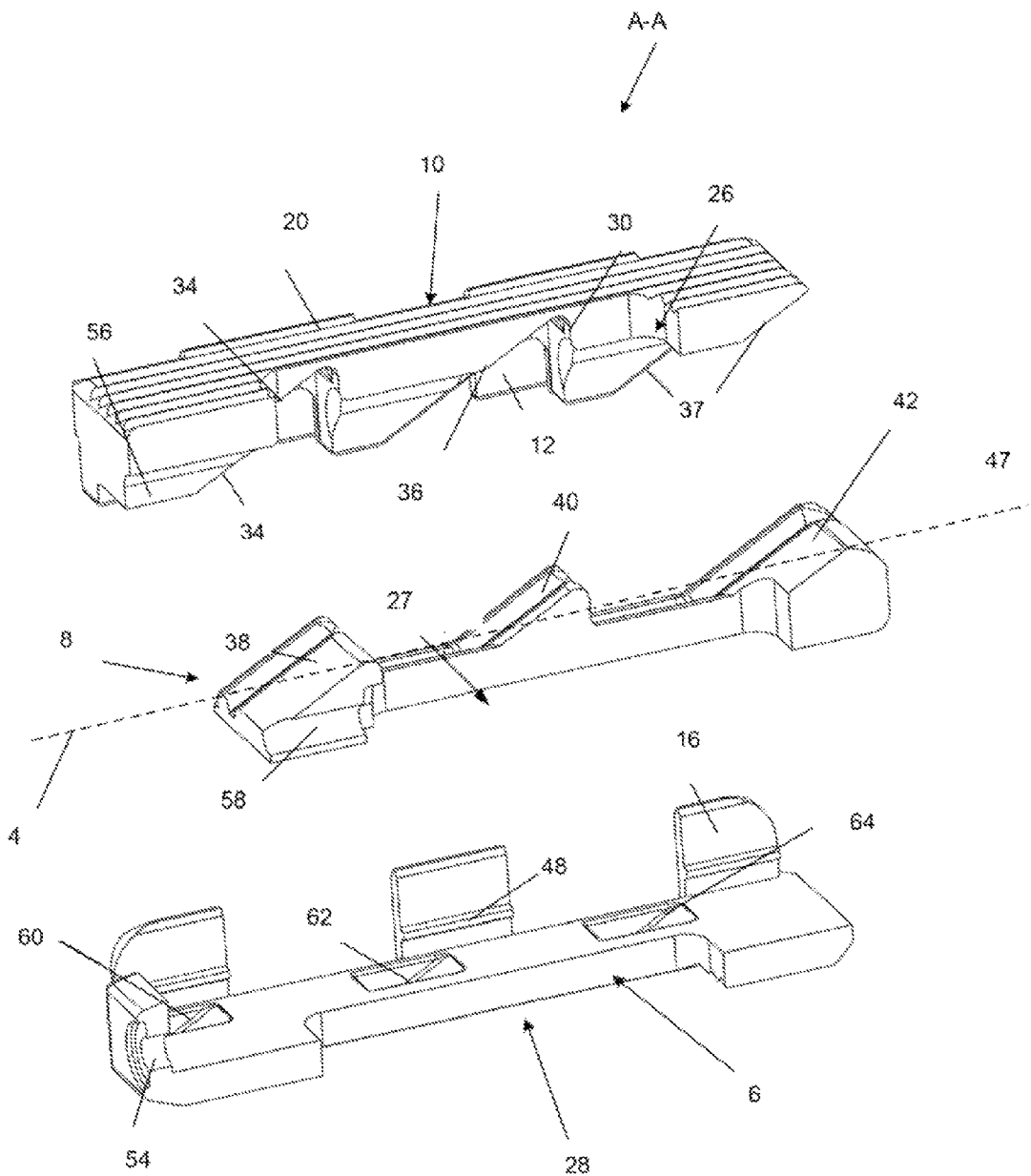

FIGS. 1a and 1b illustrate an exploded view of an expandable support device 2 that can be implanted in a bone, such as a compression fracture in a vertebra, in the intervertebral space between two vertebrae, or in soft tissue, such as a herniated intervertebral disc. The expandable support device 2 can be biocompatible. The expandable support device 2 can be used, for example, for methods of repairing vertebral bone fractures or supporting adjacent vertebral bodies for fusion. The expandable support device 2 can have a first longitudinal end and a second longitudinal end along a longitudinal axis 4.

The expandable support device 2 can have a base or bottom 6 (base and bottom are used interchangeably), a middle 8, and a top 10. The base or bottom 6 and top 10 can be or have plates, panels, struts (e.g., legs), ports, cells, and combinations thereof. The base 6 and top 10 can be configured to be slidably attachable to the middle 8. Either the top 10, the base 6, or neither, (shown in the figures as the base) can be slidably attached to the middle 8 in a plane parallel with the longitudinal axis 4. Either the top 10, the base 6, or neither, (shown in the figures as the top 10) can be slidably attached to the middle 8 in a plane substantially perpendicular to the longitudinal axis 4.

The top 10 can have one or more top stability bars 12. For example, the top stability bars 12 can extend from the lateral sides of the top 10. The top stability bars 12 can extend from the top 10 in the direction of the base 6. The base 6 can have one or more base stability grooves 14. Each top stability bar 12 can be configured to be slidably attachable to a corresponding base stability groove 14. For example, the top 10 can have two sets of one, two or more symmetrically opposite, laterally located top stability bars 12. The base 6 can have two or more sets of two symmetrically opposite, laterally located base stability grooves 14, as shown.

The base 6 can have one or more base stability bars 16. For example, the base stability bars 16 can extend from the lateral sides of the base 6. The base stability bars 16 can extend from the bas 6 in the direction of the top 10. The top 10 can have one or more top stability grooves 18. The base stability bars 16 can each be configured to be slidably attachable to a corresponding top stability groove 18. For example, the base 6 can have two sets of one, two, three (as shown) or more symmetrically opposite, laterally located base stability bars 16. The top 10 can have two or more sets of two, three (as shown) or more symmetrically opposite, laterally located top stability grooves 18, as shown.

The slidable attachment of the top 10 and base 6 can permit the base 6 to move radially (with respect to the longitudinal axis 4) relative to the top and vice versa.

The top 10 can have a high-friction and/or low-friction texture extending away from the base 6. For example, the top 10 can have one or numerous rows of top teeth 20. The bottom 6 can have a high-friction and/or low-friction texture extending away from the base 6. For example, the bottom 6 can have one or numerous rows of bottom teeth 22. The top teeth 20 and the bottom teeth 22. The teeth can be arranged to have ridges parallel with the longitudinal access, transverse the parallel axis, a non-zero and non-right angle to the longitudinal axis 4, or combinations thereof.

The top 10 can have one or more side ports and/or top ports 26. The base 6 can have one or more base ports 28 and/or side ports. The ports can be circular, square, triangular, oval, elongated in the longitudinal direction, elongated in the radial direction, or combinations thereof.

The top 10 and/or base 6 can have atraumatic edges, such as chamfered edges. The chamfers can extend along the perimeter of the base 6 and/or top 10.

The expandable support device 2 can have one, two, three or more sets of interacting wedges or ramps. The sets of ramps can be distributed substantially evenly along the length of the device, or the sets of ramps can be distributed unevenly along the length of the base 6. The ramps can all be oriented in the same direction (e.g., all ramps facing proximally, or all ramps facing distally), or can be oriented in different directions (e.g., some ramps facing distally and some ramps facing proximally).

The top 10 and/or base 6 can have a series of unidirectional and/or bidirectional ramps. The unidirectional ramps can be configured to have a ramp stop 30 at one longitudinal end of the ramp.

The middle 8 can have a series of unidirectional and/or bidrectional ramps. The unidirectional ramps can be configured to have a ramp stop 30 at one longitudinal end of the ramp.

The ramps can have ramp tongues and grooves 32. Ramp tongue and grooves 32 on corresponding ramps can be configured to slidably attach to the opposing tongues and grooves. For example, the top ramps 34, 36 can have top tongues and grooves. The middle ramps 38, 40, 42 can have middle tongues and grooves that can slidably engage the top tongues and grooves.

The ramps can have ramp angles 44 with respect to the longitudinal axis 4. The ramp angle 44 can be from about 15° to about 75°, more narrowly from about 20° to about 60°, for example about 35°.

One or more of the ramps can have a ramp stop 30. The ramp stops 30 can be configured to abut and interference fit against a corresponding ramp stop 30 on the adjacent element (i.e., the top 10 can be adjacent to the middle 8).

The base 6 (as shown) and/or top 10 can have a first side plate 46.

The base 6 can have a base rail 48. The middle 8 can have a middle rail 50. The middle rail 50 can be slidably fed onto or under the base rail 48. The base rail 48 and the middle rail 50 can constrain relative motion between the middle 8 and the base 6 to the dimension of the longitudinal axis 4.

The first side port 52 can have a first side outer port 54 on the first side plate 46. The first side port 52 can have a first side central port 56 in the top 10. The first side central port 56 can be open on the bottom 6, for example to allow the first side central port 56 to move away from the first side outer port 54 without constraining any rod or other elongated element positioned through the first side port 52. The middle 8 can have a first side inner port 58 through the middle first ramp 38. The first side outer 54, central 56, inner port 58 or a combination thereof can be internally threaded. The first side outer port 54 can form a recess in the first side plate 46, for example to receive the head of a rod.

The base 6 can have one or more seat ramps, for example, the seat ramps can be positioned to correspond with and receive one or more of the top ramps, for example when the device is in a height-contracted configuration.

The ramps can be positioned laterally symmetrically on the top 10. The ramps can be evenly distributed along the length of the top 10. The ramp seats can be positioned laterally symmetrically on the base 6. The ramps can be evenly distributed along the length of the base 6.

Figure 2A:
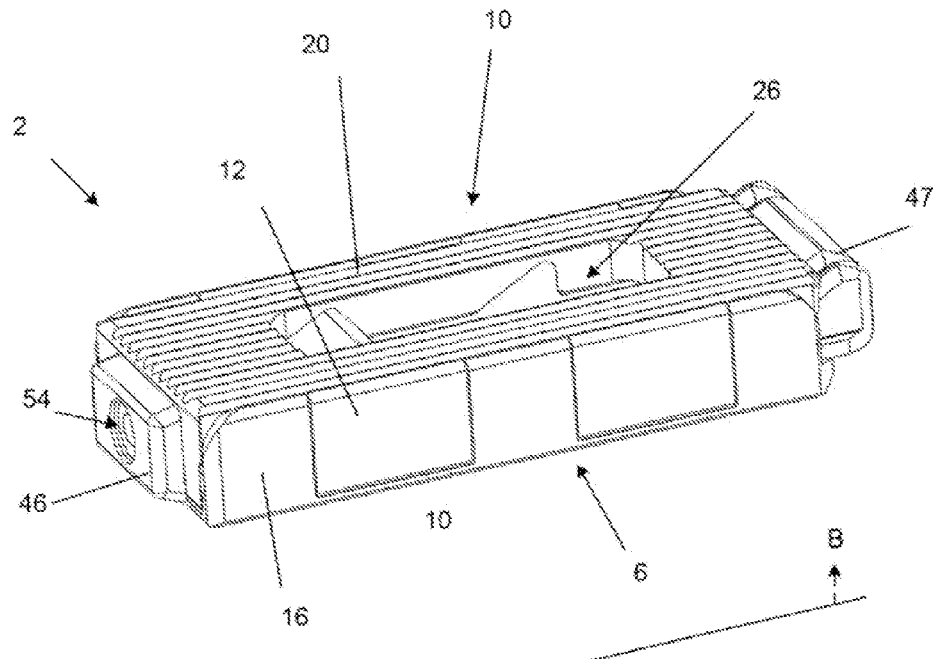
FIG. 2a illustrates a variation of the device in a height-contracted configuration.
Figure 2B:
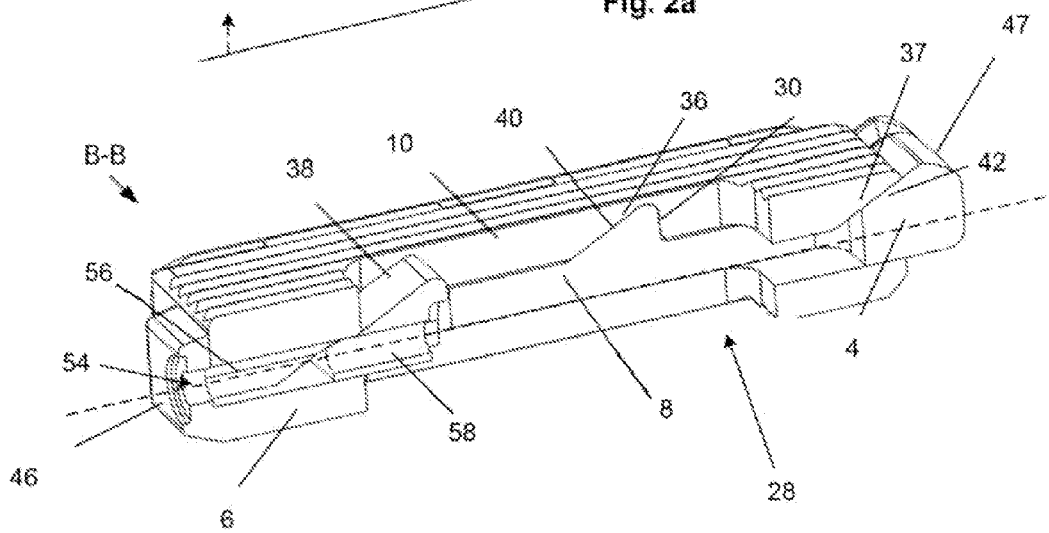

FIGS. 2a and 2b illustrate that the device 2 can have a height-contracted configuration. Top ramps can receive the middle ramps. The ramp stops of the top ramps can interference fit against the ramp stops of the middle ramps.

Figure 3A:
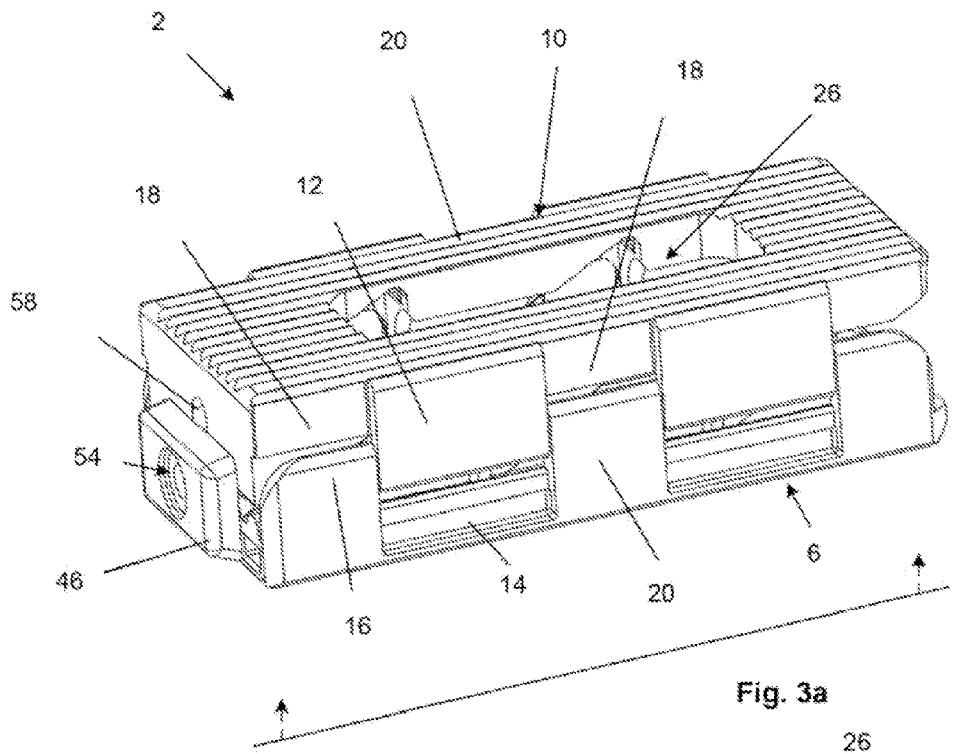
FIG. 3a illustrates a variation of the device in a height-expanded configuration.
Figure 3B:
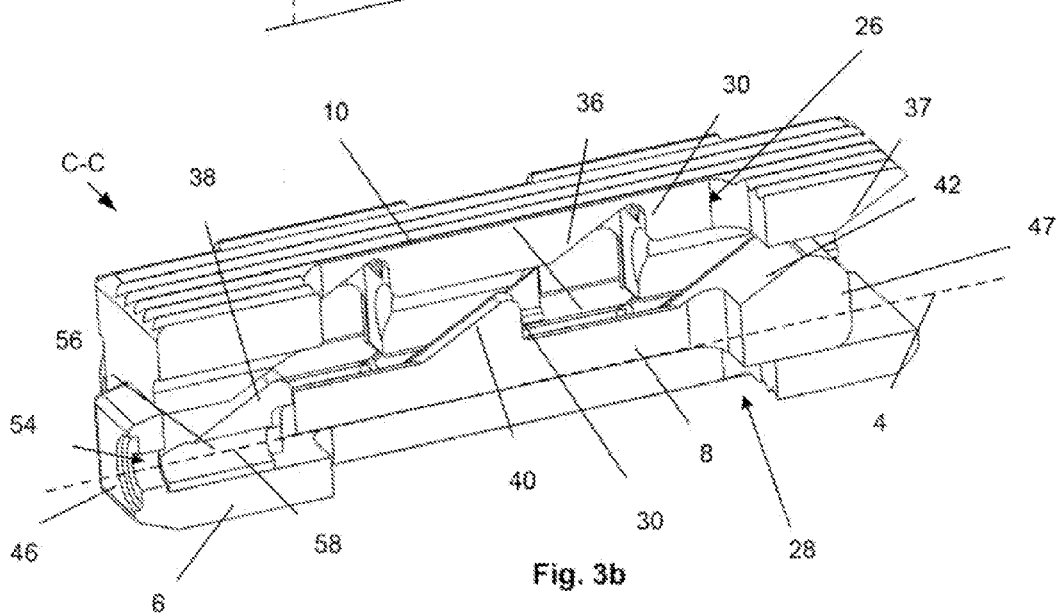

FIGS. 3a and 3b illustrate that the device can have a height-expanded configuration. The middle 8 can be slidably translated toward the first end.

The stability bar can be configured to not directly attach to the top 10 when the top stability bar 12 is translated toward the base stability groove 14, and/or the stability bars can be configured to bias inward against and frictionally hold the top 10 when the top 10 is translated into the base 6.

The top 10 and the base 6 can be pressed into or otherwise translated toward each other. For example, after implantation of the expandable support device 2, the surrounding tissue in the in vivo environment can naturally compress the expandable support device 2.

The ramps can have ratchets on their surface, in the tongue and groove or otherwise to prevent contraction once the device 2 is expanded. The device 2 can be filled by a material, and/or the deployment rod can be fixed to the first side outer port 54 and the second port.

In place of, or in addition to, the base teeth 22 and/or the top teeth 20, the respective surfaces can have high friction surfaces, for example a textured (e.g., knurled) surface and/or coated with a high friction material.

FIGS. 4a and 4b illustrate that the top port 26, middle port 27 and base port 28 substantially align transverse with the longitudinal axis 4. The top/middle/base ports form a concurrent vertical port through the device 2. The concurrent vertical port can be filled with any material disclosed herein or left empty. The concurrent vertical port can be partially obstructed by the middle 8, including the middle first ramp 38, when the device 2 is in a height-contracted configuration, as shown in FIG. 4*a*. The concurrent vertical port can be less obstructed, or substantially unobstructed when the device 2 is in a height-expanded configuration, as shown in FIG. 4*b*.

FIG. 4*a* illustrates that the middle 8 can protrude outside of the footprint of the the top 10 and bottom 6 when the device 2 is viewed from above or below in a height-contracted configuration. As shown by FIG. 4*b*, from a top or bottom view, the middle 8 can be substantially flush with the top 10 and bottom 6 when viewed from above or below when the device 2 is in a height-contracted configuration.

FIGS. 5*a* and 5*b* illustrate. the height expansion, as shown by arrow, of the top 10 away from the base 6. The height expansion can occur when the device 2 is longitudinally compressed, and/or when the middle 8 is slid with respect to the base 6 toward the first side.

FIG. 5*b* illustrates that the middle ramps slip, as shown by arrows, against the top ramps when the device 2 is expanded.

FIG. 5*c* illustrates that the middle 8 can have a second side port 68. A deployment tool and/or locking rod 70 can be inserted through the first port and the second side port 68. The deployment rod 70 can have an attached or integral deployment rod cap 72 or nut that can be outside the first port and interference fit with the wall surrounding the first port.

The rod 72 can be pulled (as shown by arrow), while a resistive force (shown by arrow) is applied to the device 2 to oppose the pulling force (to expand the device 2 rather than solely pulling the device 2 toward the user).

The deployment rod 70 or locking pin can have a pin shaft with a driver slot, for example, configured to receive a screw driver or drill bit. The pin shaft can have pin thread configured to releasably or fixedly attach to one or both of the ramp ports. The pin thread can extend along all or part of the length of the pin shaft.

The locking pin can be inserted, as shown by arrow, through the threaded ramp port. The deployment rod 70 and locking pin can be the same or different elements.

The second side ramp 74 and/or the top 10 and/or the bottom 6 can have a ramp abutment section, such as the ramp stops 30. The ramp abutment section can be configured to interference fit with and/or fixedly attach to the abutment end.

A rod detent 76 can be fitted onto or through the deployment tool or locking rod 70. The user can deploy a force against the detent 76. The detent 76 can be a clip, nut, brad, lockable slide, or combinations thereof. The detent 76 can fix to the deployment rod 70 or locking pin and interference fit against the middle 8. For example, the middle 8 can then be fixed between the rod detent 76 and the first side plate 46.

Figure 5D:
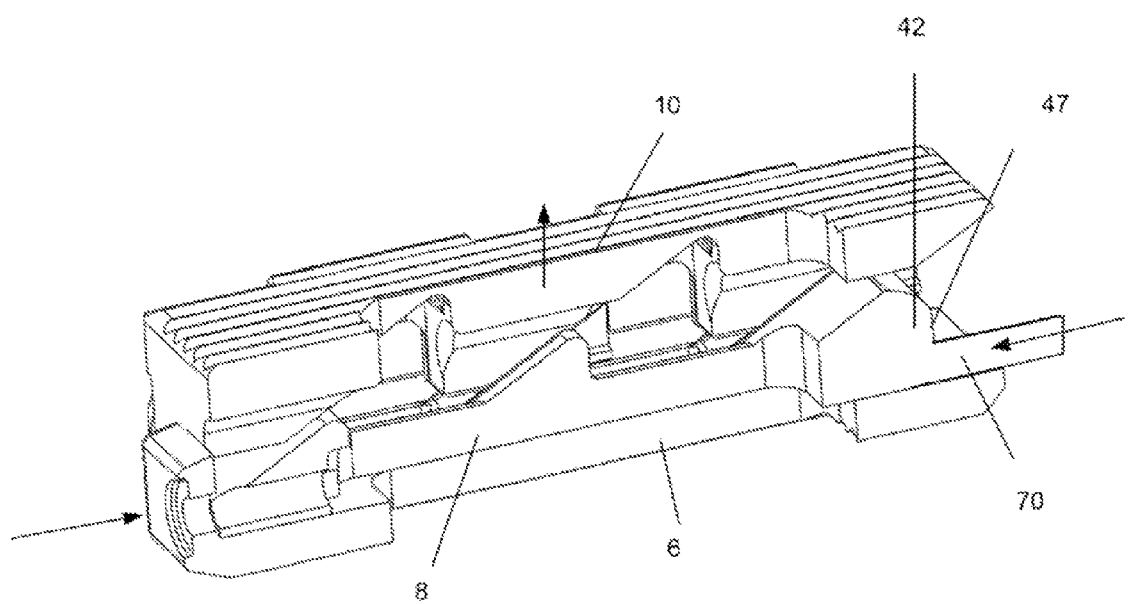

FIG. 5*d* illustrates that the deployment rod or locking pin 80 can be integral or attached to the middle 8, for example at the second side plate 47. The middle port can be unobstructed by the rod or pin.

The deployment rod 70 can be removably attached from the remainder of the device 2, for example after the device 2 is deployed. The deployment rod 70 can be used to position and expand the device 2.

FIG. 5*e* illustrates that the second side port 68 can have port thread 78 on all or a portion of the inside of the port. For example, the second side port 68 can have port thread 78 on about half of the surface of the inside of the port, for example from angles about 0 degrees to about 180 degrees when measured from a longitudinal axis 4 passing through the center of the second side port 78 (as shown), or from about 0 degrees to about 90 degrees and then again from about 180 degrees to about 270 degrees.

The deployment rod or locking pin 80 can have rod/pin thread 82 on a portion of the surface of the rod or pin 80 corresponding to and substantially equal to or less than the portion of the surface of the inside of the port covered by port thread 78. For example, the rod or pin 80 can have rod/pin thread 82 on about half of the surface of the outside of the rod or pin 80, for example from angles about 0 degrees to about 180 degrees when measured from a longitudinal axis 4 passing through the center of the rod or pin 80 (as shown), or from about 0 degrees to about 90 degrees and then again from about 180 degrees to about 270 degrees.

The non-threaded portion of the surface of the rod 80 can be angularly aligned with the threaded portion of the surface of the second side port 68

FIG. 5*f* illustrates that the rod or pin 80 can be translated into or through the second side port 68. The rod/pin thread 82 can slidably pass across the inner surface of the second side port 68 not having port thread 78. The port thread 78 can slide past the outer surface of the second side port 68 not having port thread 78.

FIG. 5*g* illustrates that when the rod or pin 80 is at a desired position, the rod or pin 80 can be rotated to align the rod/pin thread 82 with the port thread 78. The rod or pin 80 can be translatably fixed with respect to the second side port 68.

The partial-thread shown on the second side port 68 in FIGS. 5*e* through 5*g* can be on a separate nut rotatably attached to the second side port 68. For example, once the rod or pin 80 is in a desired position, the nut can be rotated with respect to the rod or pin 80 to longitudinally fix the position of the rod or pin 80 with respect to the nut and therefore the second side port 68.

A biocompatible adhesive or epoxy can be applied to the pin thread 82, threaded ramp port, abutment end, ramp abutment section, or combinations thereof.

One, two or more locking pin channels can be inserted longitudinally into the expandable support device 2. One, two or more locking pins 80 can be inserted into the same or separate ports, for example during or after deployment of the remainder of the expandable support device 2. The locking pins 80 can prevent overexpansion and/or overcompression and/or disassembly of the expandable support device 2.

Once the device 2 is expanded and/or before expansion, the ramps can have locking pins 80 therethrough.

The locking pin 80 can be cylindrical. The locking pin channel and locking pin port can have elongated cross-sections, such as an oval or rectangular or oblong cross-sections. The locking pin 80 can be free to move vertically within a range of motion within the locking pin port.

The locking pin 80 can be a substantially similar shape and size as the locking pin channel. The locking pin 80 can be substantially unmovable within the locking pin port. The locking pin 80, locking pin channel and locking pin port can all have elongated cross-sections, such as an oval or rectangular or oblong cross-sections.

The ramps can have first fixing teeth or ratchets. The first fixing teeth can be in contact with the top 10 and/or the bottom 6. The top and/or the bottom can have second fixing teeth.

The first fixing teeth can mechanically interact with the second fixing teeth to allow relative translation in a first direction. The first fixing teeth and the second fixing teeth can interact to obstruct (e.g., by interference fitting the first fixing teeth against the second fixing teeth) relative translation in a second direction. For example, the fixing teeth can obstruct the top ramps from moving one way, for example not allowing the device to contract, and obstruct the top from moving closer to the bottom. Also for example, the fixing teeth can allow relative translation of the side ramps toward each other, for example, to allow the top to move away from the bottom.

The second side ramp 74 can have a first end. The first end can be configured to dissect tissue. The first end can have a blunt or sharp point.

The second side ramp 74 can have a tool connector, such as an externally and/or internally threaded cylinder extending longitudinally from the second side ramp away from the first side ramp. The tool connector can be configured to removably attach to a deployment tool.

The first fixing teeth can unidirectionally interference fit the second fixing teeth. The unidirectional interference fit of the first fixing teeth and the second fixing teeth can substantially impede or prevent the opposite ramps from moving longitudinally away from each other, for example, therefore impede or preventing compression of the top toward the bottom and vice versa.

The unidirectional interference fit of the first fixing teeth and the second fixing teeth can allow the opposite ramps to move longitudinally toward each other, for example, therefore allowing the top to expand away from the bottom and vice versa.

An external deployment tool can be attached to the first side plate 46 and the second port 68 of the side of the device, and apply a compressive force across the device 2. The base 6 and top 10 can expand away from each other, as shown by arrows.

When the expandable support device 2 is in a deployed configuration in vivo, the expandable support device 2 can be partially or substantially filled with a liquid, gel, or solid (e.g., in small parts or granules) filler material, or combinations thereof, such as bone morphogenic powder or any other material disclosed herein or combinations thereof. The filler material can contact or be in near contact with the surrounding tissue near the edge of the ports The expandable support devices 2 can have textured and/or porous surfaces for example, to increase friction against bone surfaces, and/or promote tissue ingrowth. The expandable support devices 2 can be coated with a bone growth factor, such as a calcium base.

The expandable support device 2 can be covered by a thin metal screen, for example over at least the top and/or base ports. The thin metal screen can expand and/or open when the expandable support device 2 expands.

Any or all elements of the expandable support device 2 and/or other devices or apparatuses described herein can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyethylene teraphathalate (PET)/polyester (e.g., DACRON® from E. I. Du Pont de Nemours and Company, Wilmington, Del.), polypropylene, (PET), polytetrafluoroethylene (PTFE), expanded PTFE (ePTFE), poly ether ketone (PEK), polyether ether ketone (PEEK), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), polylactic acid (PLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone) any of the other materials listed herein or combinations thereof. Examples of radiopaque materials are barium sulfate, zinc oxide, titanium, stainless steel, nickel-titanium alloys, tantalum and gold.

Any or all elements of the expandable support device 2 and/or other devices or apparatuses described herein, can be, have, and/or be completely or partially coated with agents and/or a matrix a matrix for cell ingrowth or used with a fabric, for example a covering (not shown) that acts as a matrix for cell ingrowth. The matrix and/or fabric can be, for example, polyester (e.g., DACRON® from E. I. Du Pont de Nemours and Company, Wilmington, Del.), polypropylene, PTFE, ePTFE, nylon, extruded collagen, silicone or combinations thereof.

The expandable support device 2 and/or elements of the expandable support device 2 and/or other devices or apparatuses described herein and/or the fabric can be filled, coated, layered and/or otherwise made with and/or from cements, fillers, glues, and/or an agent delivery matrix known to one having ordinary skill in the art and/or a therapeutic and/or diagnostic agent. Any of these cements and/or fillers and/or glues can be osteogenic and osteoinductive growth factors.

Examples of such cements and/or fillers includes bone chips, demineralized bone matrix (DBM), calcium sulfate, coralline hydroxyapatite, biocoral, tricalcium phosphate, calcium phosphate, polymethyl methacrylate (PMMA), biodegradable ceramics, bioactive glasses, hyaluronic acid, lactoferrin, bone morphogenic proteins (BMPs) such as recombinant human bone morphogenetic proteins (rhBMPs), other materials described herein, or combinations thereof.

The agents within these matrices can include any agent disclosed herein or combinations thereof, including radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 inhibitors (e.g., VIOXX® from Merck & Co., Inc., Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostoglandin $E_2$ Synthesis in Abdominal Aortic Aneurysms, *Circulation*, Jul. 6, 1999, 48-54; Tambiah et al, Provocation of Experimental Aortic Inflammation Mediators and Chlamydia Pneumoniae, *Brit. J. Surgery* 88 (7), 935-940; Franklin et al, Uptake of Tetracycline by Aortic Aneurysm Wall and Its Effect on Inflammation and Proteolysis, *Brit. J. Surgery* 86 (6), 771-775; Xu et al, Sp1 Increases Expression of Cyclooxygenase-2 in Hypoxic Vascular Endothelium, *J. Biological Chemistry* 275 (32) 24583-24589; and Pyo et al, Targeted Gene Disruption of Matrix Metalloproteinase-9 (Gelatinase B) Suppresses Development of Experimental Abdominal Aortic Aneurysms, *J. Clinical Investigation* 105 (11), 1641-1649 which are all incorporated by reference in their entireties.

The expandable support devices 2 can be laser cut, machined, cut by wire electrical discharge machining ("EDM") or made by other suitable techniques. The expandable support device 2 can be cut in a fully contracted or unexpanded configuration or may be cut in a partially opened pattern, then loaded (e.g., crimped) onto a deployment tool 84 (e.g., balloon). The loaded expandable support device 2 can have a smaller profile while plastically deforming the struts past their limits.

The expandable support device 2 can be longitudinally segmented. Multiple expandable support devices 2 can be attached first end to second end, and/or a single expandable support device 2 can be severed longitudinally into multiple expandable support devices 2.

Method of Use

Figure 6:
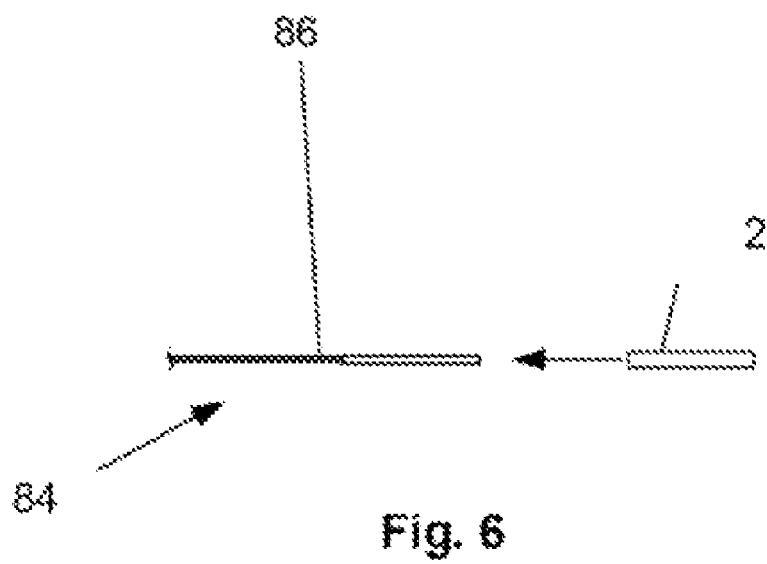
FIGS. 6 and 7 illustrate a variation of a method for using a delivery system for the expandable support element.

FIG. 6 illustrates that the expandable support device 2 can be loaded in a collapsed (i.e., contracted) configuration onto a deployment tool 84. The deployment tool 84 can be configured to removably attach to the first side ramp and the second side ramp. One or more deployment tools can be configured to control the position of the expandable support device 2 (e.g., to rigidly attach to the expandable support device 2) and/or to longitudinally compress the second side ramps 74, and/or to deploy one or more locking pins in the expandable support device 2. The deployment tool 84 can include a rigid or flexible catheter 86.

Figure 7:
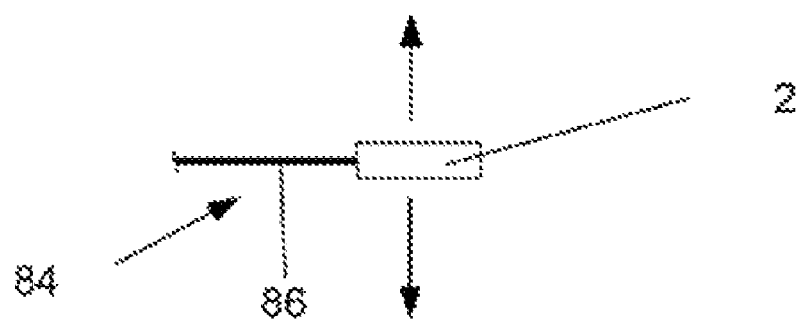

FIG. 7 illustrates that the deployment tool 86 can longitudinally compress the expandable support device 2, for example causing the expandable support device 2 to vertically expand as shown by arrows.

Figures 8, 9:
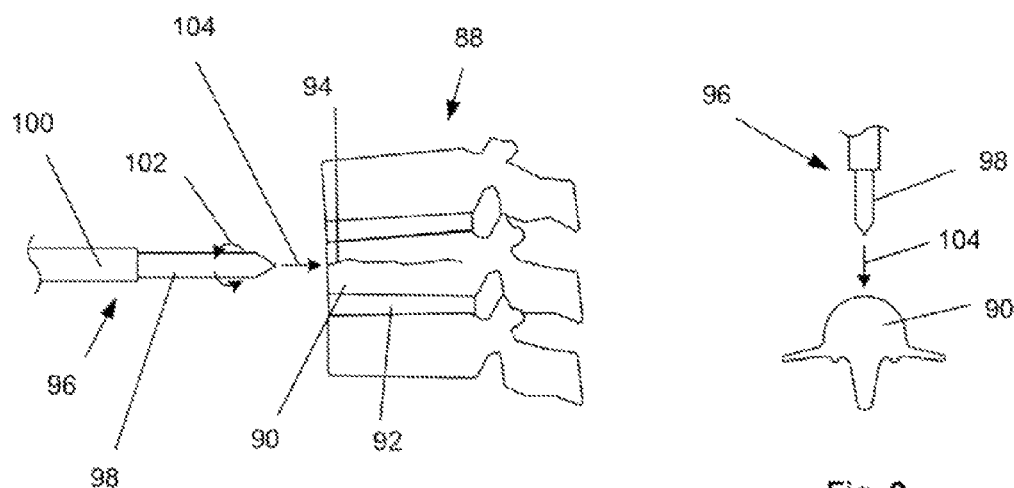
FIGS. 8 through 10 illustrate a variation of a method for accessing a damage site in the vertebra.

FIGS. 8 (side view) and 9 (top view) illustrate a vertebral column 88 that can have one or more vertebra 90 separated from the other vertebra 90 by discs 92. The vertebra 90 can have a damage site 94, for example a compression fracture.

An access tool 96 can be used to gain access to the damage site 94 and or increase the size of the damage site 94 to allow deployment of the expandable support device 2. The access tool 96 can be a rotating or vibrating drill 98 that can have a handle 100. Optionally, the drill 98 may oscillate, as shown by arrows 102. The drill 98 can then be translated, as shown by arrow 104, toward and into the vertebra 90 so as to pass into the damage site 94.

Figure 10:
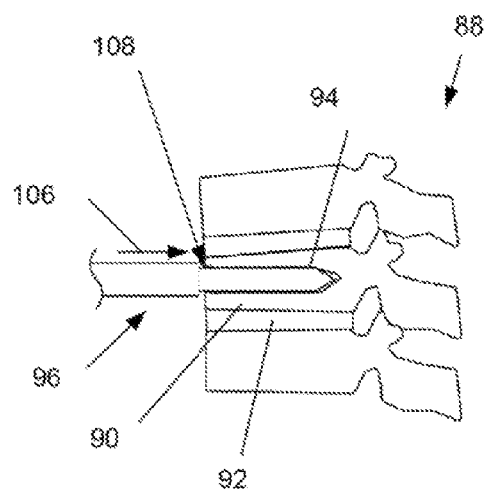

FIG. 10 illustrates that the access tool 96 can be translated, as shown by arrow 106, to remove tissue at the damage site 94. The access tool 96 can create an access port 108 at the surface of the vertebra 90. The access port 108 can open to the damage site 94. The access tool 96 can then be removed from the vertebra 90.

Figure 11:
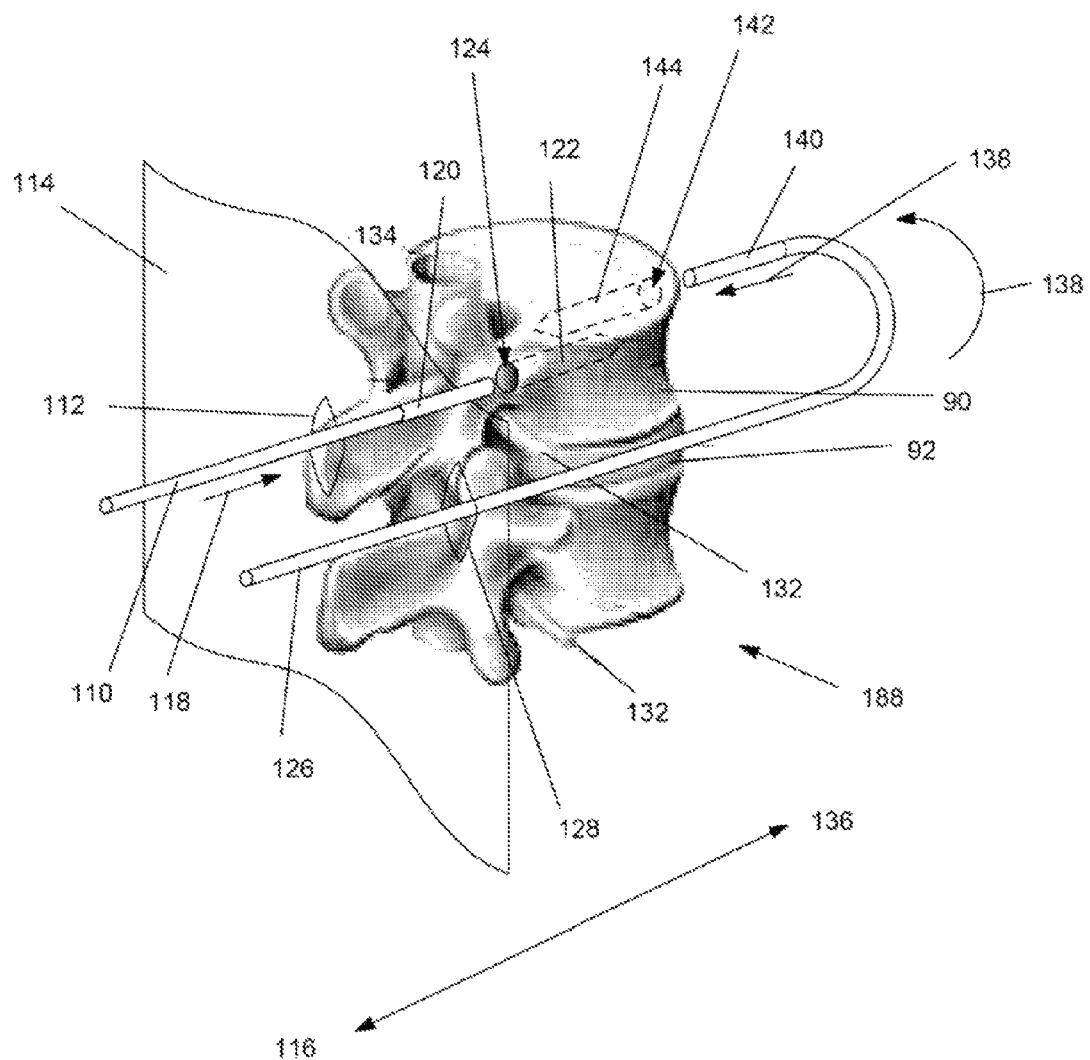
FIG. 11 illustrates two methods for delivering expandable support devices to the vertebral column.

FIG. 11 illustrates that a first deployment tool 110 can enter posteriorly through the subject's back. The first deployment tool 110 can enter through a first incision 112 in the skin 114 on the posterior side 116 of the subject near the vertebral column 88. The first deployment tool 110 can be translated, as shown by arrow 118, to position a first expandable support device 120 into a first damage site 122. The first access port 124 can be on the posterior side 116 of the vertebra 90.

A second deployment tool 126 can enter through a second incision 128 (as shown) in the skin 114. The second incision 130 may be posterior (as shown) or may be anterior, lateral, posterior lateral, or the like. The second deployment tool 126 can be translated through muscle (not shown), around nerves 132, the spinal cord 134, and anterior 136 of the vertebral column 88. The second deployment tool 126 can be steerable. The second deployment tool 126 can be steered, as shown by arrow 138, to align the distal tip of the second expandable support device 140 with a second access port 142 on a second damage site 144. The second access port 142 can face anteriorly 136. The second deployment tool can translate, as shown by arrow 146, to position the second expandable support device 140 in the second damage site 144.

As illustrated, the vertebra 90 can have multiple damage sites and expandable support devices deployed therein. The expandable support devices can be deployed from the anterior 136, posterior 116, both lateral, superior, inferior, any angle, or combinations of the directions thereof. Of course, a single device may be deployed from one direction rather than multiple devices from multiple directions.

Figure 12:
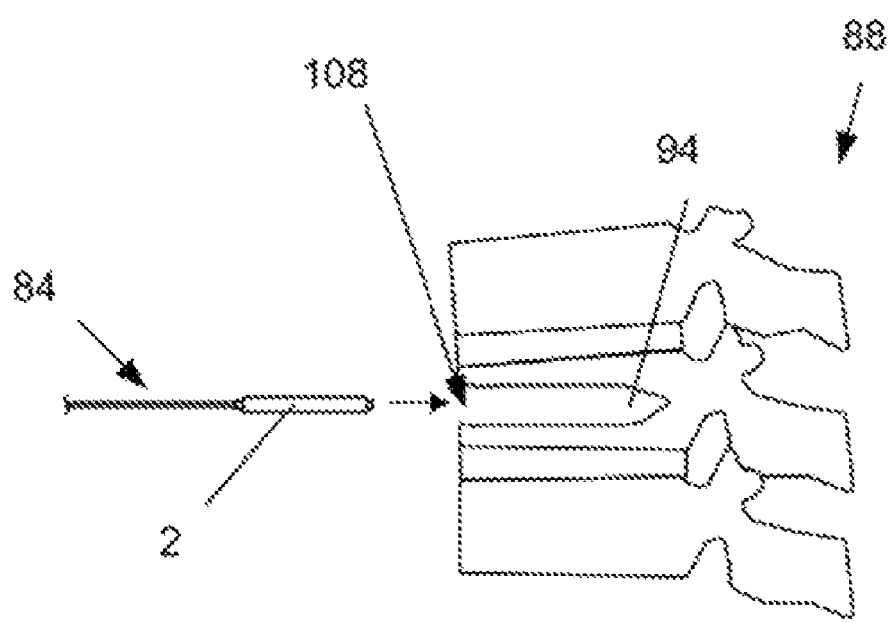
FIGS. 12 through 17 illustrate various methods for deploying the expandable support device into the damage site in the vertebra.
Figure 13:
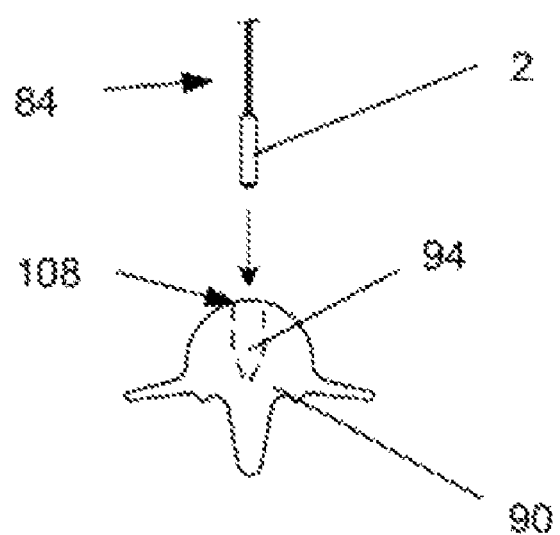
Figure 14:
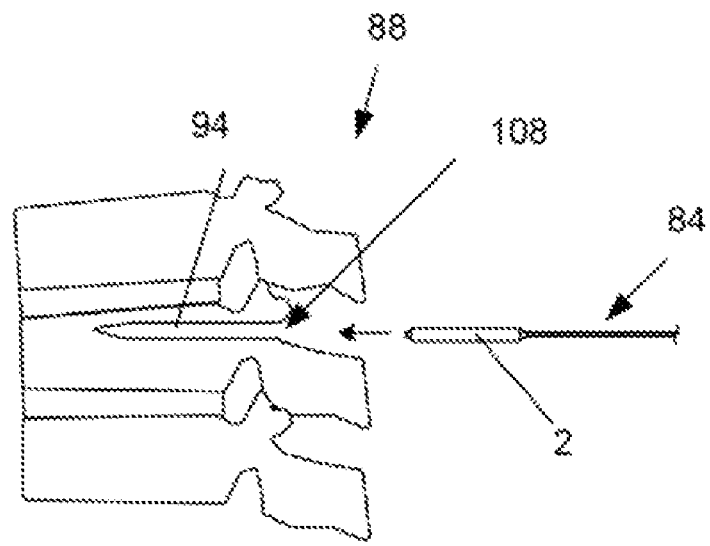
Figure 15:
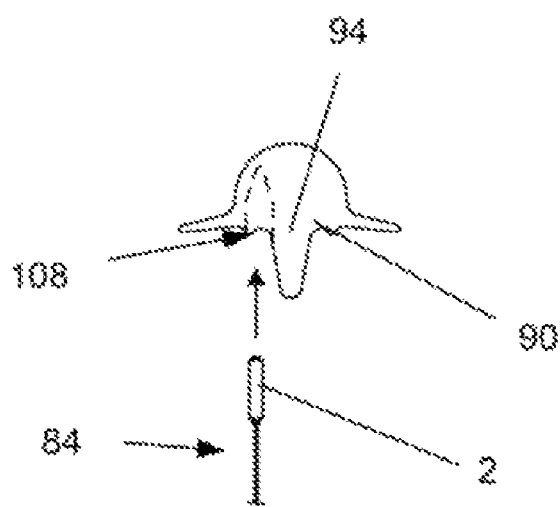

FIGS. 12 and 13 illustrate translating, as shown by arrow, the deployment tool 84 loaded with the expandable support device 2 through the access port 108 from the anterior side 136 of the vertebral column 88. FIGS. 14 and 15 illustrate that the deployment tool 84 can be deployed from the posterior side 116 of the vertebral column 88. The deployment tool 84 can be deployed off-center, for example, when approaching the posterior side 116 of the vertebral column 88.

Figure 16:
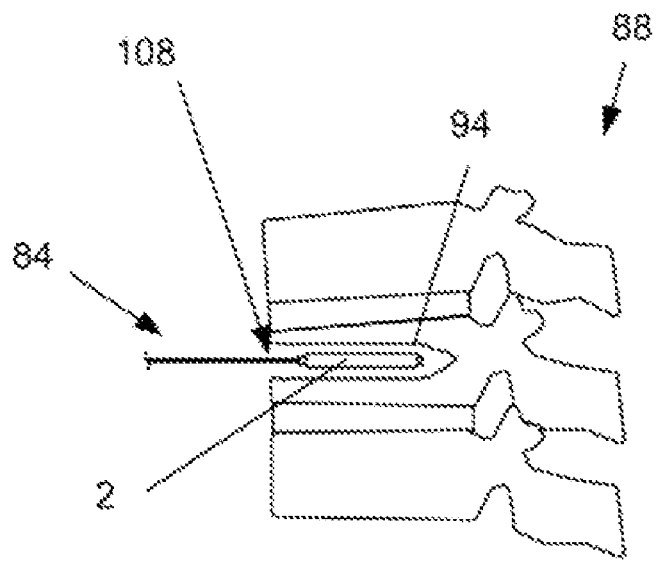

FIG. 16 illustrates that deployment tool 84 can position the expandable support device 2 in the vertebra 90 and into the damage site 94.

Figure 17:
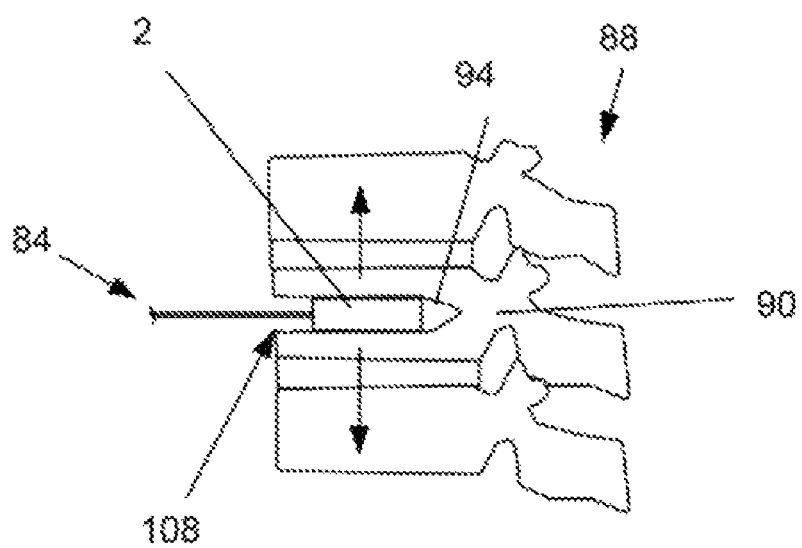

FIG. 17 illustrates that the expandable support device 2 can be longitudinally compressed (i.e., vertically expanded) until the expandable support device 2 is substantially fixed to the vertebra 90. The expandable support device 2 can reshape the vertebral column 88 to a more natural configuration during expansion of the device.

Figure 18:
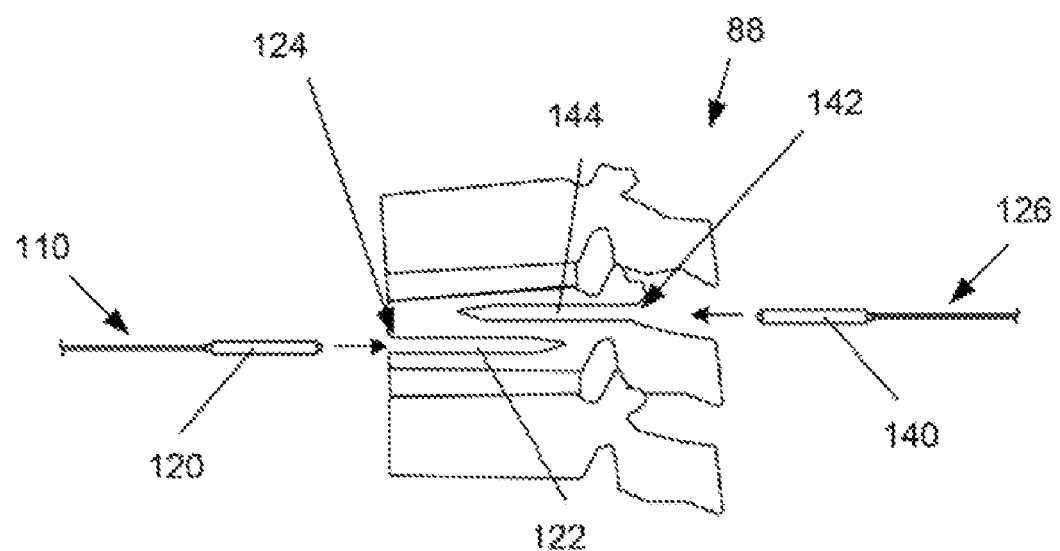
FIGS. 18 and 19 illustrate a variation of a method for deploying one or more expandable support devices into one or more damage sites in the vertebra.
Figure 19:
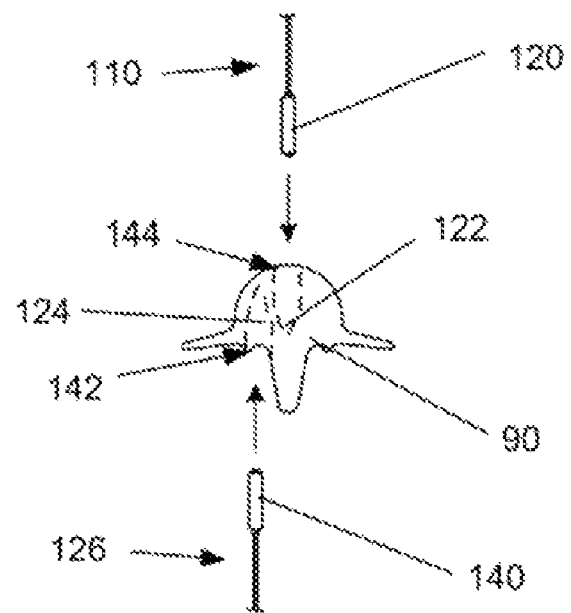

FIGS. 18 and 19 illustrate that first and second deployment tools 110 and 126 can position and deploy first and second expandable support devices 120 and 140 simultaneously, and/or in the same vertebra 90 and into the same or different damage sites 122 and 144.

Figure 20:
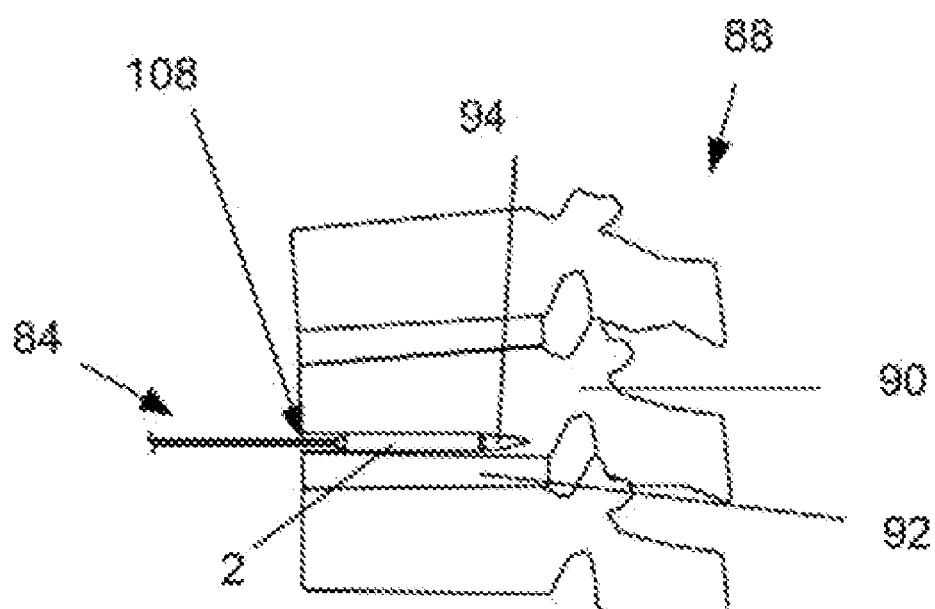
FIG. 20 illustrates a variation of a method for deploying the expandable support device into the damage site in the vertebra.

FIG. 20 illustrates that the access port 108 can be made close to the disc 92, for example when the damage site 94 is close to the disc 92. The deployment tool 84 can be inserted through the access port 108 and the expandable support device 2 can be deployed as described supra.

Figure 21:
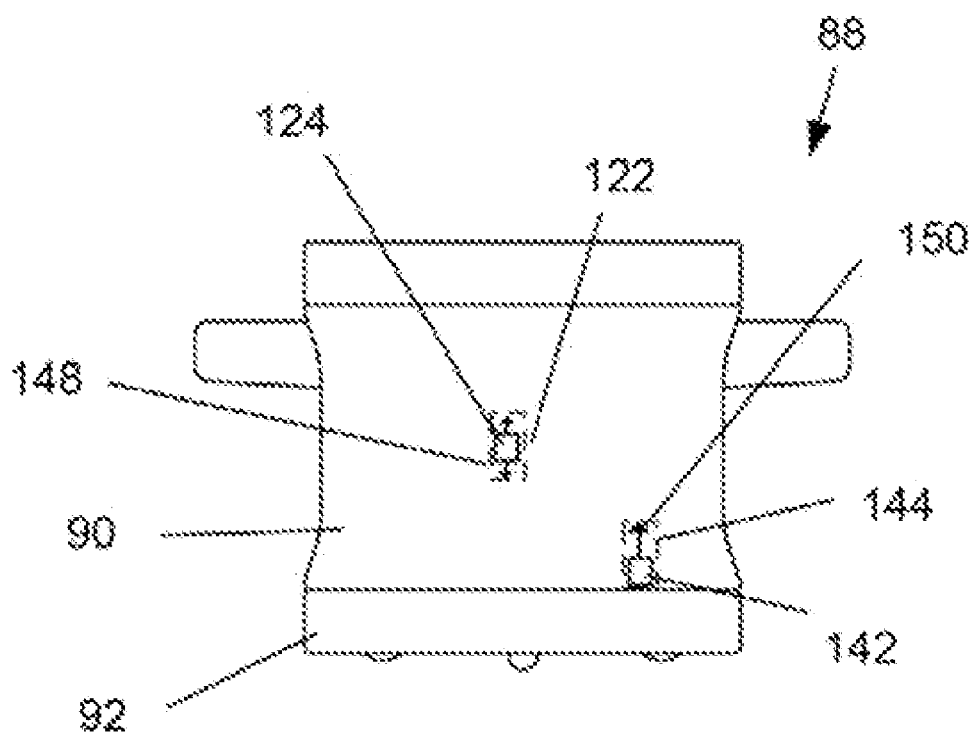
FIG. 21 illustrates variations of methods for deploying the expandable support device into the damage site in the vertebra.

FIG. 21, a front view of the vertebral column 88, illustrates that more than one expandable support device 2 can be deployed into a single vertebra 90. For example, a first expandable support device (not shown) can be inserted through a first access port 124 and deployed in a first damage site 122, and a second expandable support device (not shown) can be inserted through a first access port 124 and deployed in a second damage site 144.

The first access port 124 can be substantially centered with respect to the first damage site 122. The first expandable support device (not shown) can expand, as shown by arrows 148, substantially superiorly and inferiorly, aligned with the center of the first access port 124. The second access port 142 can be substantially not centered with respect to the second damage site 144. The second expandable support device can substantially anchor to a side of the damage site 94 and/or the surface of the disc 92, and then expand, as shown by arrows 150, substantially directionally away from the disc 92.

Figure 22:
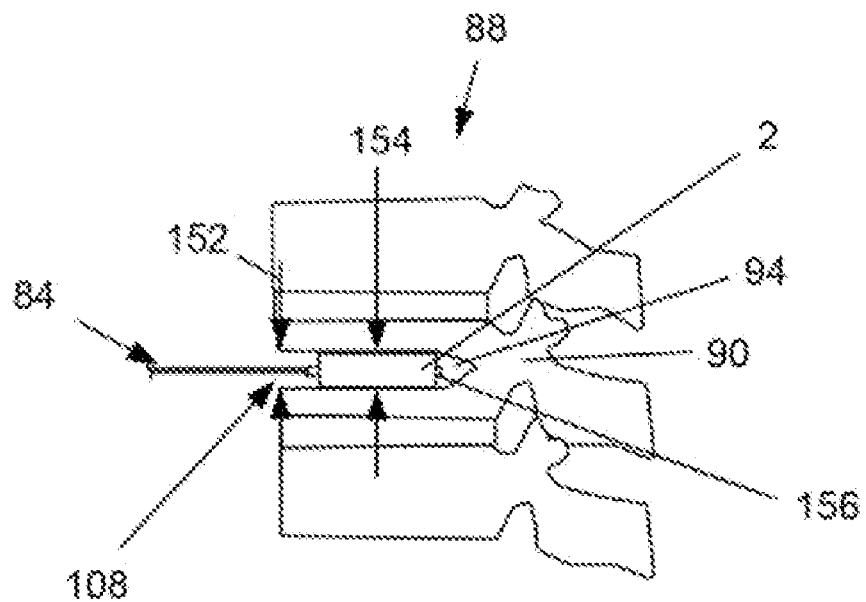
FIGS. 22 and 23 illustrate a variation of a method for deploying the expandable support device into the damage site in the vertebra.

FIG. 22 illustrates that when compressive tension from the deployment tool 84 is no longer exerted on the expandable support device 2, the expandable support device 2 can be self-locking and/or a fixation pin can be inserted before, during or after the compressive tension is stopped. The expandable support device 2 can then be substantially fixed to the vertebra 90 at the damage site 94. For example, the expandable support device 2 can be subject to biomechanical compression within one or between two vertebrae 90.

The access port 108 can have an access port diameter 152. The access port diameter 152 can be from about 1.5 mm (0.060 in.) to about 40 mm (2 in.), for example about 8 mm (0.3 in.). The access port diameter 152 can be a result of the size of the access tool 96 and in the unexpanded expandable support device 2. After the expandable support device 2 is deployed the damage site 94 can have a deployed diameter 154. The deployed diameter 154 can be from about 1.5 mm (0.060 in.) to about 120 mm (4.7 in.), for example from about 10 mm (0.4 in.) to about 20 mm (0.8 in.), or from about 12 mm (0.47 in.) to about 16 mm (0.63 in.). The deployed diameter 154 can be greater than, equal to, or less than the access port diameter 152.

Figure 23:
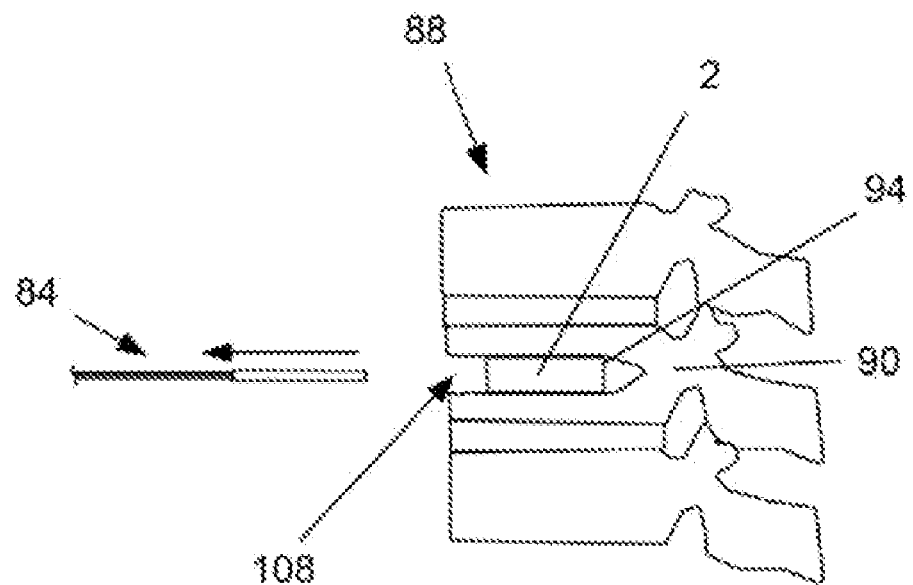

FIG. 23 illustrates that the deployment tool 84 can be removed, as shown, from the vertebra 90 after the expandable support device 2 is deployed.

Figure 24:
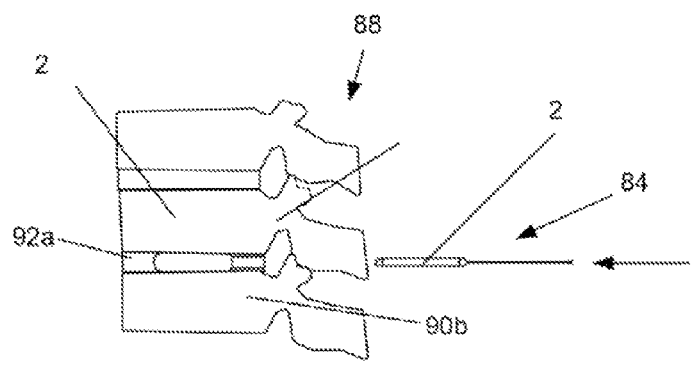
FIGS. 24 through 27 illustrate a variation of a method for deploying the expandable support device between adjacent vertebrae.

FIG. 24 illustrates that the expandable support device 2 can be loaded onto the deployment tool 84. The expandable support device 2 can be positioned adjacent to the disc 92. The disc 92 can be between a first vertebra 90a and a second vertebra 90b.

Figure 25:
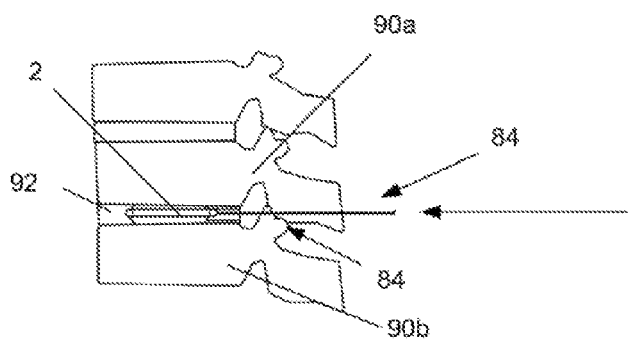

FIG. 25 illustrates that the expandable support device 2 can be inserted into the disc 92, for example into the nuclear space or into the annular space. Removal of none, part or all of the nucleus and/or annulus can be performed before placing the expandable support device 2 in the disc 92.

Figure 26:
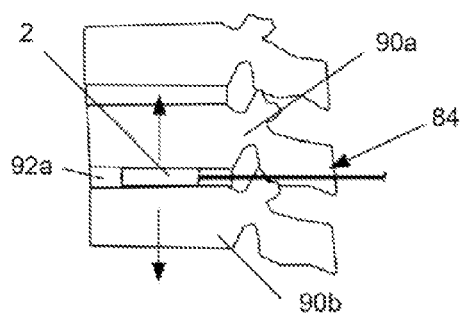

FIG. 26 illustrates that the expandable support device 2 can be radially expanded, as shown by arrows, in the space of the disc 92a. Rough texturing, ingrowth matrix, teeth, or combinations thereof on the top or bottom of the expandable support device 2 can engage the first or second vertebrae 90a or 90b or both. The expandable support device 2 can fuse or fix the first vertebra 90a to the second vertebra 90b. The expandable support device 2 can increase the gap between the first vertebra 90a and the second vertebra 90b (e.g., to restore proper or original biomechanics and/or anatomical geometry).

Figure 27:
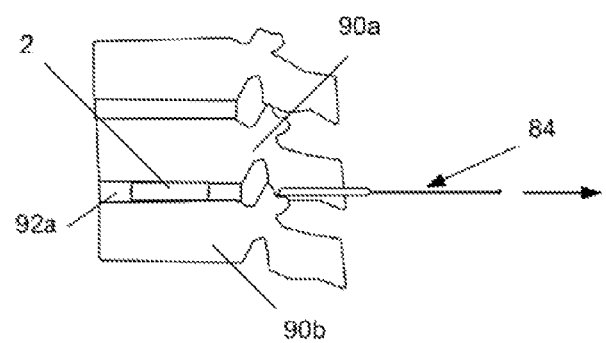

FIG. 27 illustrates that the deployment tool 84 can be disconnected from the expandable support device 2. The deployment tool 84 can be removed from the space of the disc 92a with or without the expandable support device 2.

Figure 28:
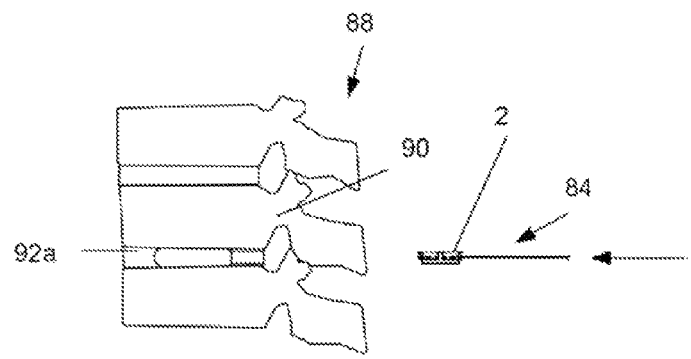
FIGS. 28 through 31 illustrate a variation of a method for deploying the expandable support device between adjacent vertebrae.
Figure 29:
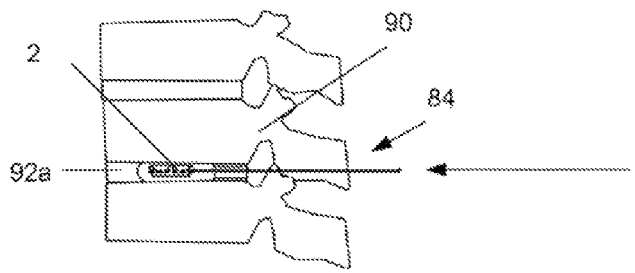
Figure 30:
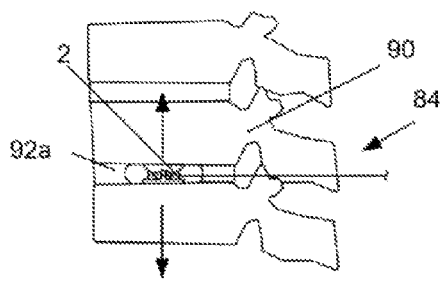
Figure 31:
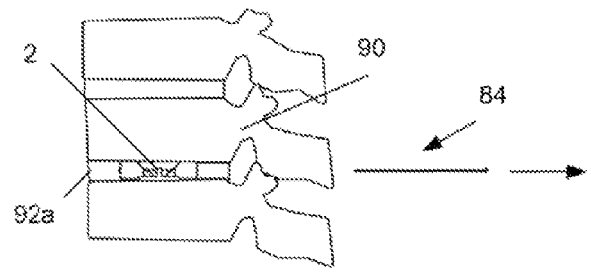

FIGS. 28 through 31 illustrate a method of deploying the variation of the expandable support device 2. FIG. 28 illustrates that the expandable support device 2 can be attached to the deployment tool 84. The expandable support device 2 can be positioned adjacent to the target site, such as the disc space 92a and/or a vertebra 90. FIG. 29 illustrates that the deployment tool 84 can translate and rotate the expandable support device 2 to the target site. FIG. 30 illustrates that the expandable support device 2 can be longitudinally compressed and radially expanded, as shown by arrows. FIG. 31 illustrates that the deployment tool 84 can be separated from the expandable support device 2. The deployment tool 84 can be removed from the target site. The expandable support device 2 can be left in the target site or removed.

Figure 32:
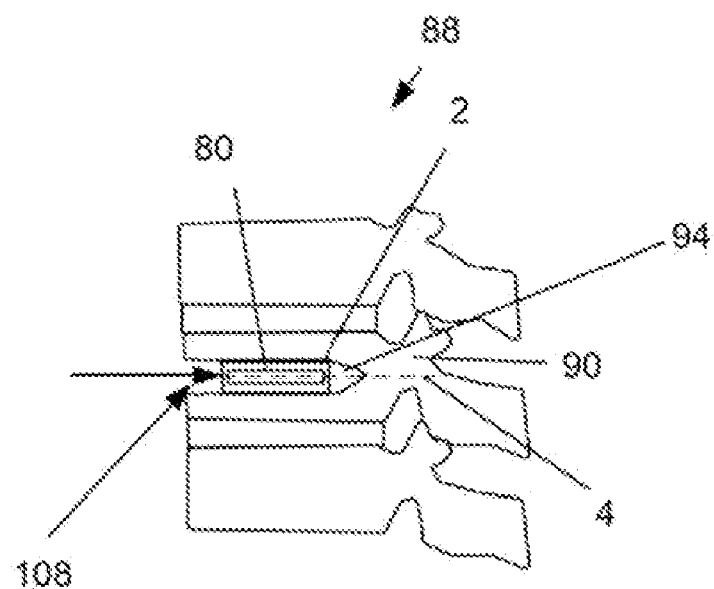
FIGS. 32 and 33 illustrate a variation of a method for deploying a locking pin into the expandable support device in the damage site in the vertebra.
Figure 33:
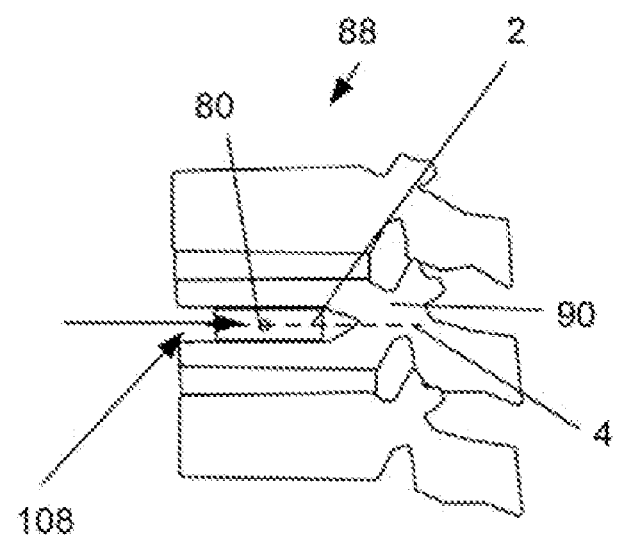

FIGS. 32 and 33 illustrate that a locking pin 80 can be inserted, as shown by arrow, into the deployed expandable support device 2, for example, after the expandable support device 2 is deployed in the vertebra 90. The locking pin 80 can prevent the expandable support device 2 from collapsing after the expandable support device 2 is deployed in the vertebra 90. The locking pin 80 can form an interference fit with the expandable support device 2 or may include features to hold the locking pin in place.

Figure 34A:
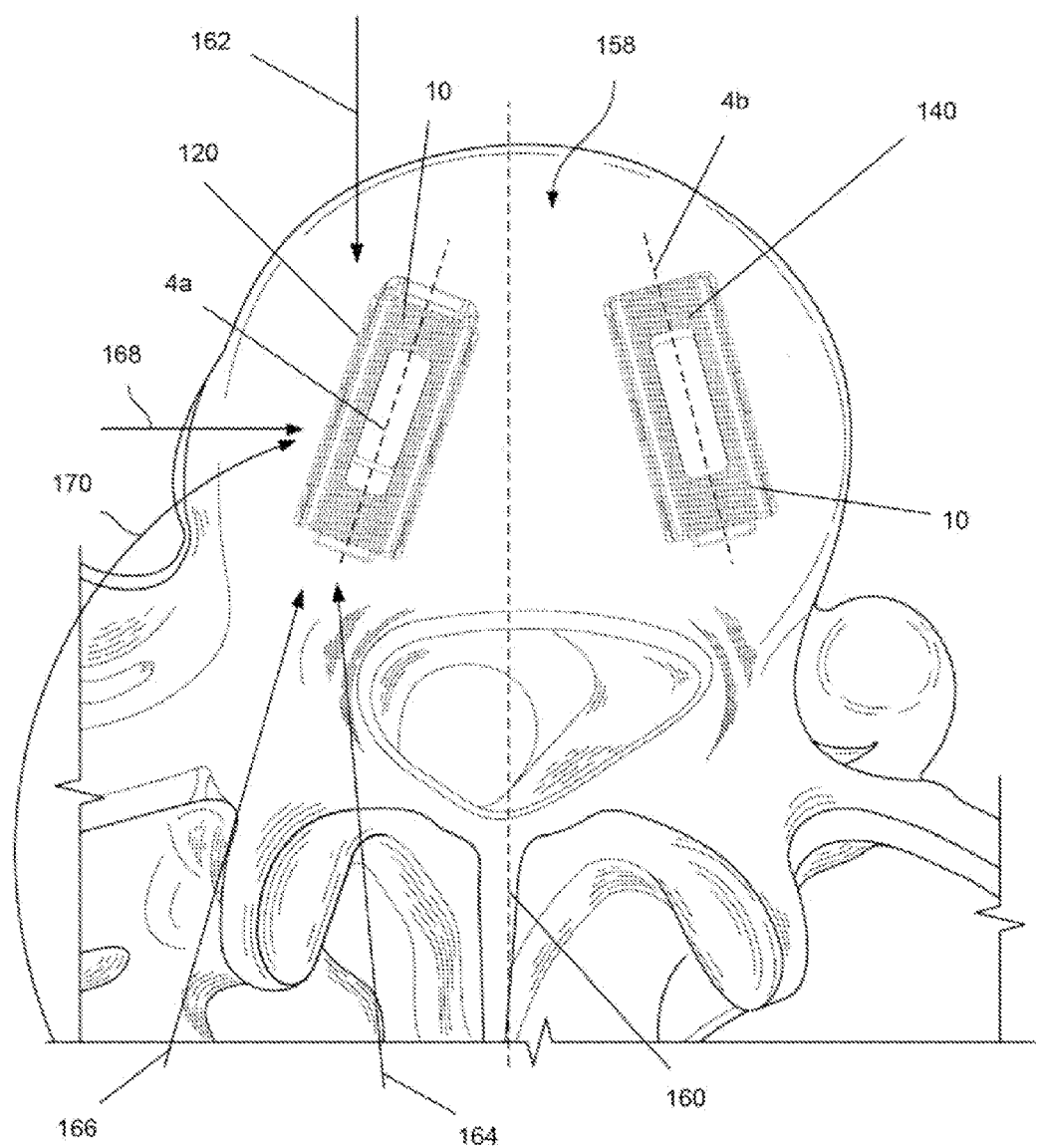
FIGS. 34a and 34b illustrate variations of methods for inserting one or more devices into one or more target sites.

FIG. 34a illustrates that one, two or more devices 2, such as a first device 120 and a second device 140, can be inserted, deployed and/or implanted the target site, such as in a vertebral body 158 or on a vertebral body 158 (e.g., between adjacent vertebral bodies). The devices 2 can be oriented so the longitudinal axes 4 of the devices 2 are substantially parallel with an anterior-posterior axis 160 of the patient.

The first device 120 can be oriented so the first device longitudinal axis 4a can be substantially parallel with the anterior-posterior axis 160.

The second device 140 can be oriented so the second device longitudinal axis 4b can be substantially parallel with the anterior-posterior axis 160. The second device 140 can be positioned in a substantially symmetric location and angular orientation to the first device 120 with respect to the anterior-posterior axis 160.

After placed into position at the target site, the device 2 can be longitudinally contracted and radially expanded. For example, as shown, the second device 140 has been radially expanded, and the first device 120 has been delivered to the target site and not yet radially expanded. Multiple devices can be delivered concurrently or sequentially. Multiple devices can be radially expanded sequentially or concurrently.

The devices can be inserted with a surgical technique such as an Anterior Lumbar Interbody Fusion (ALIF), shown by arrow 162, Posterior Lumbar Interbody Fusion (PLIF), shown by arrow 164, Transforaminal Lumbar interbody Fusion (TLIF), shown by arrow 166, a direct linear lateral delivery, as shown by arrow 168, a curvilinear lateral delivery initially inserted posteriorly, as shown by arrow 170, or other methods or combinations thereof.

Operative planning and templating can be performed using MRI and CAT imaging scans to determine what size device fits the patient's anatomy and pathology.

The disc (i.e., intervertebral) space or other target site can then be prepared. For PLIF procedures, the vertebrae can be accessed through an incision in the patient's back (i.e., posterior to the vertebrae). Depending on the number of vertebral levels to be fused, about a 3-6 inch incision can be made in the patient's back. The spinal muscles can then be retracted (or separated), for example, to allow access to the target vertebral discs. The lamina can then be removed (i.e., a laminectomy), for example, to be able to see and access the nerve roots. The facet joints, which can lie directly over the nerve roots, can be trimmed, for example, to allow more room for the nerve roots. The target disc and surrounding tissue can then be removed and the bone surfaces of adjacent vertebrae can be prepared (e.g., cleaned, abraded, debrided, textured, scored, coated with osteogenic powders or other agents, or combinations thereof).

The devices 2 can then be inserted into the target site. One or more devices 2 and/or bone graft (e.g., autograft, allograft, xenograft), BMP, or combinations thereof, can be inserted into the target site or disc space, for example, to promote fusion between the vertebrae. Additional instrumentation (e.g., rods or screws) can also be used at this time to further stabilize the spine.

TLIF can include delivering the device 2 to the spine in a path more from the side of the spinal canal than a PLIF approach and through a midline incision in the patient's back. TLIF can reduce the amount of surgical muscle dissection and can minimizes nerve manipulation required to access the vertebrae, discs and nerves.

TLIF can include removing disc material from the spine and inserting the device(s) 2 and bone graft, BMP, screws, rods, or combinations thereof.

ALIF is performed inserting from the front (anterior) of the body, usually through a 3-5 inch incision in the lower abdominal area or on the side. This incision may involve cutting through, and later repairing, the muscles in the lower abdomen.

A mini open ALIF approach can be performed. A mini open ALIF can preserves the muscles and allow access to the front of the spine through an incision. This approach maintains abdominal muscle strength and function and can be used to fuse the L5-S1 disc space, for example Once the incision is made and the vertebrae are accessed, and after the abdominal muscles and blood vessels have been retracted, the disc material can be removed. The surgeon can then insert the devices 2 and/or bone graft, rods, screws, BMP, or combinations thereof, for example to stabilize the spine and facilitate fusion.

The target site for the device(s) 2 can be between sacral, lumbar, thoracic, cervical vertebrae, or combinations thereof. The target site can be between other bones, such as intercostal (between ribs), in the knee, elbow, wrist, ankle, or combinations thereof.

Figure 34B:
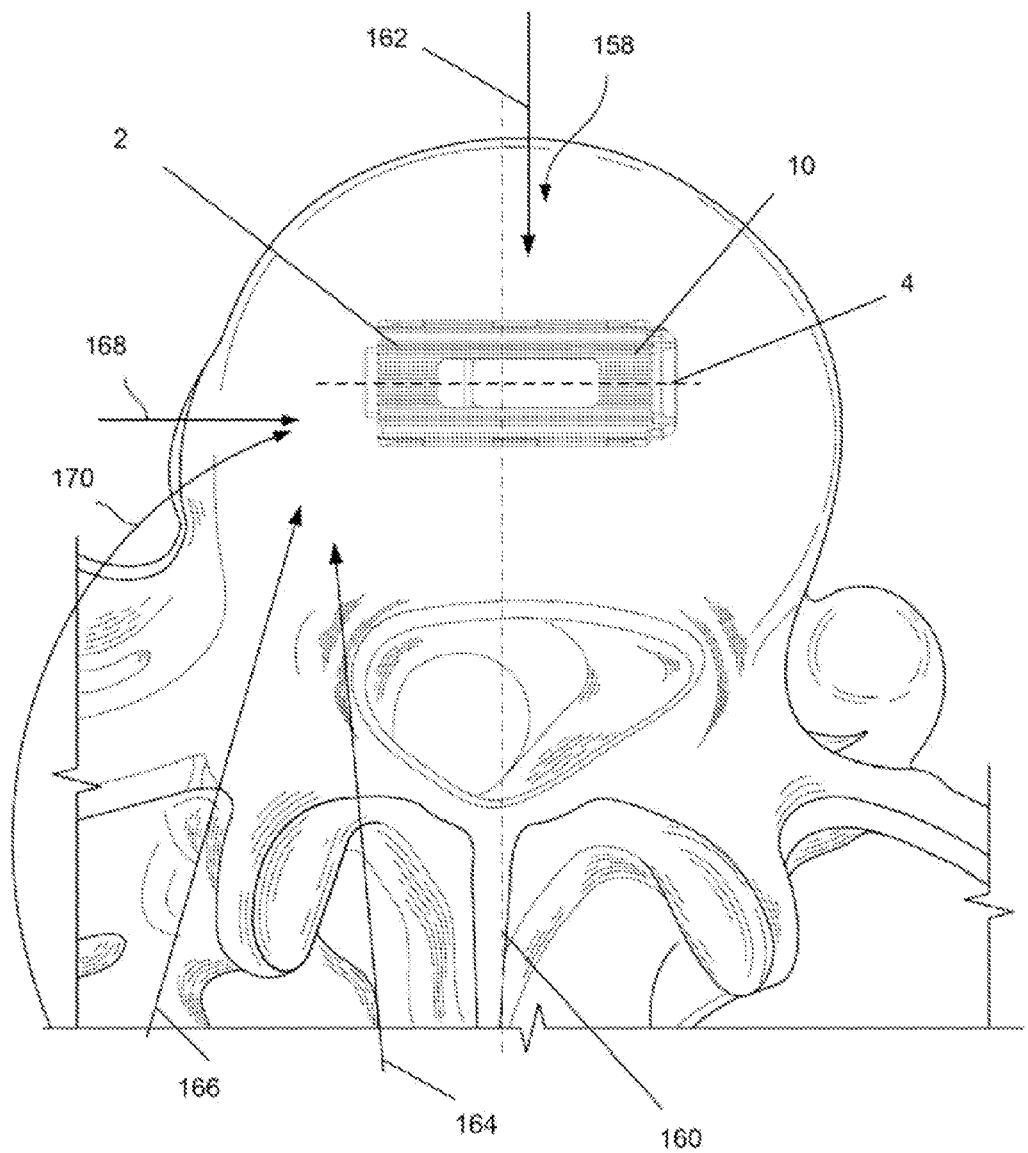

FIG. 34*b* illustrates that one (as shown) or more devices 2 can be inserted into the target site, such as in a vertebral body 158 or on a vertebral body 158 (e.g., between adjacent vertebral bodies). The longitudinal axis 4 of the device 2 can be oriented substantially perpendicular to the anterior-posterior axis 160 (i.e., parallel to a lateral axis).

PCT Application No. US2005/034,728, Publication No. WO 2006/068,682, entitled "Expandable Support Device and Method of Use", filed 26 Sep. 2005, and U.S. Provisional Patent Application No.: 60/612,728, filed on 24 Sep. 2004, are herein incorporated by reference in their entireties.

It is apparent to one skilled in the art that various changes and modifications can be made to this disclosure, and equivalents employed, without departing from the spirit and scope of the invention. Elements shown with any variation are exemplary for the specific variation and can be used on other variations within this disclosure. Any elements described herein as singular can be pluralized (i.e., anything described as "one" can be more than one). Any species element of a genus element can have the characteristics or elements of any other species element of that genus. The above-described configurations, elements or complete assemblies and methods and their elements for carrying out the invention, and variations of aspects of the invention can be combined and modified with each other in any combination.

We claim:

1. An expandable implant device comprising an intervertebral spacer comprising:
   a first load-bearing element;
   a second load-hearing element;
   a sliding element slidably attached to the first load-hearing element and the second load-bearing element,
   wherein the sliding element has first and second sliding element ramps and
   wherein the first load-bearing element has first and second load bearing ramps, and
   wherein the first and second sliding element ramps are configured to press against the first and second load-bearing ramps, respectively, when the sliding element is translated with respect to the first load-hearing element, and
   wherein the translation of the sliding element with respect to the first load-bearing element causes the first load-bearing element to move away from the second load-bearing element, and
   wherein the first load-bearing element and the second load-bearing element and the sliding element have respective centrally located openings therethrough, and the respective openings at least partially align with each other along a direction from the first load-bearing element to the second load-bearing element.

2. The device of claim 1, wherein the first sliding element ramp has a first tooth configured to allow unidirectional sliding against the first load-bearing element.

3. The device of claim 2, wherein the first load-bearing ramp is configured to allow unidirectional sliding against the first sliding element.

4. The device of claim 1. higher comprising a locking pin.

5. The device of claim 4, wherein the locking, pin is attached to the first load-bearing element.

6. The device of claim 4, wherein the locking pin is attached to the sliding element.

7. The device of claim 1, wherein the first load-bearing element has a third load-bearing ramp.

8. The device of claim 1, wherein the sliding element has a third sliding element ramp.

* * * * *